United States Patent [19]
Nash et al.

[11] Patent Number: 6,143,762
[45] Date of Patent: Nov. 7, 2000

[54] TETRAHYDROISOQUINOLINE DERIVATIVES AND THEIR PHARMACEUTICAL USE

[75] Inventors: David John Nash, Little Walden; Geoffrey Stemp, Bishop's Stortford, both of United Kingdom

[73] Assignee: SmithKline Beecham, plc, Brentford, United Kingdom

[21] Appl. No.: 09/242,200

[22] PCT Filed: Aug. 8, 1997

[86] PCT No.: PCT/EP97/04408

§ 371 Date: Feb. 11, 1999

§ 102(e) Date: Feb. 11, 1999

[87] PCT Pub. No.: WO98/06699

PCT Pub. Date: Feb. 19, 1998

[30] Foreign Application Priority Data

Aug. 14, 1996 [GB] United Kingdom ................ 9617079
Mar. 5, 1997 [GB] United Kingdom ................ 9704523

[51] Int. Cl.[7] ............... A61K 31/505; A61K 31/47; C07D 239/02; C07D 217/22; C07D 217/00
[52] U.S. Cl. ............... 514/307; 514/275; 514/307; 514/308; 514/310; 544/332; 546/141; 546/143; 546/146
[58] Field of Search ............... 546/141, 143, 546/146; 514/275, 307, 308, 310; 544/332

[56] References Cited

U.S. PATENT DOCUMENTS

| | | | |
|---|---|---|---|
| 4,925,850 | 5/1990 | George et al. | 514/307 |
| 5,294,621 | 3/1994 | Russell | 514/301 |
| 6,046,210 | 4/2000 | Stemp et al. | 514/307 |

FOREIGN PATENT DOCUMENTS

| | | |
|---|---|---|
| WO 95 16674 | 6/1995 | WIPO . |
| WO 96 02246 | 2/1996 | WIPO . |
| WO 96 30333 | 10/1996 | WIPO . |

OTHER PUBLICATIONS

Chemical Abstract, vol. 107, No. 11, Sep. 14, 1987, abstract No. 089337, Patsenko et al. "Interaction of simple tetahydroisoquinolines with opiate and high affinity dopamine (D3) receptors of rat striatum", XP002048675.

Boyfield et al. "A novel series of 2–aminotetralins with high affinity and selectivity for the dopamine D3 receptor" Bioorg. Med. Chem. Lett.97; vol. 7 (15); pp. 1995–1998, XP002048674.

Primary Examiner—Mukund J. Shah
Assistant Examiner—Ben Schroeder
Attorney, Agent, or Firm—Nora Stein-Fernandez; Janice F. Williams; Charles M. Kinzig

[57] ABSTRACT

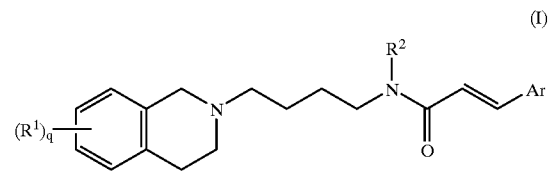

Compounds of formula (I), wherein $R^1$ represents a substituent selected from: a hydrogen or halogen atom; a hydroxy, cyano, nitro, trifluoromethyl, trifluoromethoxy, trifluoromethanesulfonyloxy, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulphonyl, $C_{1-4}$alkylsulphonyloxy, $C_{1-4}$alkylsulphonyl$C_{1-4}$alkyl, arylsulphonyl, arylsulphonyloxy, arylsulphonyl$C_{1-4}$alkyl, $C_{1-4}$alkylsulphonamido, $C_{1-4}$alkylamido, $C_{1-4}$alkylsulphonamido$C_{1-4}$alkyl, $C_{1-4}$alkylamido$C_{1-4}$alkyl, arylsulphonamido, arylcarboxamido, arylsulphonamido$C_{1-4}$alkyl, arylcarboxamido$C_{1-4}$alkyl, aroyl, aroyl$C_{1-4}$alkyl, or aryl$C_{1-4}$alkanoyl group; a group $R^3OCO(CH_2)_p$, $R^3CON(R^4)(CH2)p$, $R^3R^4NCO(CH_2)_p$ or $R^3R^4NSO_2(CH_2)_p$ where each of $R^3$ and $R^4$ independently represents a hydrogen atom or a $C_{1-4}$alkyl group or $R^3R^4$ forms part of a $C_{3-6}$azacyloalkane or $C_{3-6}$(2-oxo)azacycloalkane ring and p represents zero or an integer from 1 to 4; or a group $Ar^1Z$, wherein $Ar^1$ represents an optionally substituted phenyl ring or an optionally substituted 5- or 6-membered aromatic heterocyclic ring and Z represents a bond, O, S, or $CH_2$; represents a hydrogen atom or a $C_{1-4}$alkyl group; q is 1 or 2; Ar represents an optionally substituted phenyl ring or an optionally substituted 5- or 6-membered aromatic ring; or an optionally substituted bicyclic aromatic or heteroaromatic ring system; and salts thereof. Compounds of formula (I) and their salts have affinity for dopamine receptors, in particular the $D_3$ receptor, and thus potential in the treatment of conditions wherein modulation of the $D_3$ receptor is beneficial, e.g. as antipsychotic agents.

10 Claims, No Drawings

TETRAHYDROISOQUINOLINE DERIVATIVES AND THEIR PHARMACEUTICAL USE

The present invention relates to novel tetrahydroisoquinoline derivatives, processes for their preparation, pharmaceutical compositions containing them and their use in therapy, as modulators of dopamine $D_3$ receptors, in particular as antipsychotic agents.

U.S. Pat. No. 5,294,621 describes tetrahydropyridine derivatives of the formula:

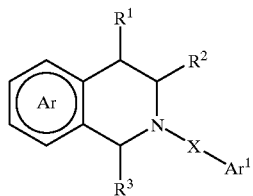

wherein

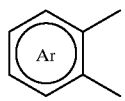

is an optionally substituted thienyl or optionally substituted phenyl ring; $R^1$, $R^2$ and $R^3$ are each inter alia hydrogen; X is inter alia $(CH_2)mNR^7CO$; m is 2–4; and $Ar^1$ is an optionally substituted heterocyclic ring or an optionally substituted phenyl ring. The compounds are said to be useful as antiarrhythmic agents.

We have now found a class of tetrahydroisoquinoline derivatives which have affinity for dopamine receptors, in particular the $D_3$ receptor, and thus potential in the treatment of conditions wherein modulation of the $D_3$ receptor is beneficial, eg as antipsychotic agents.

In a first aspect the present invention provides compounds of formula (I):

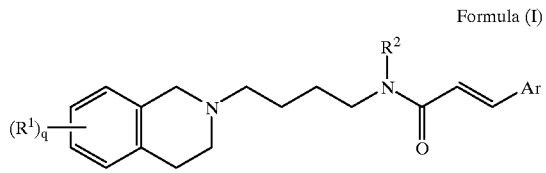

Formula (I)

wherein:
$R^1$ represents a substituent selected from: a hydrogen or halogen atom; a hydroxy, cyano, nitro, trifluoromethyl, trifluoromethoxy, trifluoromethanesulfonyloxy, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulphonyl, $C_{1-4}$alkylsulphonyloxy, $C_{1-4}$alkylsulphonyl$C_{1-4}$alkyl, arylsulphonyl, arylsulphonyloxy, arylsulphonyl$C_{1-4}$alkyl, $C_{1-4}$alkylsulphonamido, $C_{1-4}$alkylamino, $C_{1-4}$alkylsulphonamido$C_{1-4}$alkyl, $C_{1-4}$alkylamido$C_{1-4}$alkyl, arylsulphonamido, arylcarboxamido, arylsulphonamido$C_{1-4}$alkyl, arylcarboxamido$C_{1-4}$alkyl, aroyl, aroyl$C_{1-4}$alkyl, or aryl$C_{1-4}$alkanoyl group; a group $R^3OCO(CH_2)_p$, $R^3CON(R^4)(CH2)p$, $R^3R^4NCO(CH_2)_p$ or $R^3R^4NSO_2(CH_2)_p$ where each of $R^3$ and $R^4$ independently represents a hydrogen atom or a $C_{1-4}$alkyl group or $R^3R^4$ forms part of a $C_{3-6}$azacyloalkane or $C_{3-6}$(2-oxo)azacycloalkane ring and p represents zero or an integer from 1 to 4; or a group $Ar^1Z$, wherein $Ar^1$ represents an optionally substituted phenyl ring or an optionally substituted 5- or 6-membered aromatic heterocyclic ring and Z represents a bond, O, S, or $CH_2$;

$R^2$ represents a hydrogen atom or a $C_{1-4}$alkyl group;

q is 1 or 2;

Ar represents an optionally substituted phenyl ring or an optionally substituted 5- or 6-membered aromatic heterocyclic ring; or an optionally substituted bicyclic aromatic or heteroaromatic ring system;

and salts thereof.

In the compounds of formula (I) above an alkyl group or moiety may be straight or branched. Alkyl groups which may be employed include methyl, ethyl, n-propyl, n-butyl, n-pentyl, n-hexyl and any branched isomers thereof such as isopropyl, t-butyl, sec-pentyl, and the like.

When $R^1$ represents an aryl$C_{1-4}$alkoxy, arylsulphonyl, arylsulphonyloxy, arylsulphonyl$C_{1-4}$alkyl, arylsulphonamido, arylcarboxamido, arylsulphonamido$C_{1-4}$alkyl, arylcarboxamido$C_{1-4}$alkyl, aroyl, aroyl$C_{1-4}$alkyl, or aryl$C_{1-4}$alkanoyl group, the aryl moiety may be selected from an optionally substituted phenyl ring or an optionally substituted 5- or 6-membered heterocyclic ring. In the group $R^1$ an aryl moiety may be optionally substituted by one or more substituents selected from hydrogen, halogen, amino, cyano, $C_{1-4}$alkyl, $C_{1-4}$alkylamino, $C_{1-4}$dialkylamino, $C_{1-4}$alkylamido, $C_{1-4}$alkanoyl, or $R^5R^6NCO$ where each of $R^5$ and $R^6$ independently represents a hydrogen atom or $C_{1-4}$alkyl group.

A halogen atom present in the compounds of formula (I) may be fluorine, chlorine, bromine or iodine.

When q is 2, the substituents $R^1$ may be the same or different. Preferably q represents 1.

An optionally substituted 5- or 6-membered heterocyclic aromatic ring, as defined for either of the groups Ar or $Ar^1$ may contain from 1 to 4 heteroatoms selected from O, N or S. When the ring contains 2–4 heteroatoms, one is selected from O, N and S and the remaining heteroatoms are preferably N. Examples of 5 and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl and pyrazolyl.

Examples of bicyclic aromatic or heteroaromatic ring systems for Ar include naphthyl, quinolinyl, indolyl, indazolyl, benzofuranyl, benzothienyl, benzimidazolyl, benzoxazolyl, quinoxalinyl, quinazolinyl, cinnolinyl, benzothiazolyl and pyridopyrrolyl.

The rings Ar and $Ar^1$ may each independently be optionally substituted by one or more substituents selected from: a hydrogen or halogen atom, a hydroxy, cyano, nitro, $C_{1-4}$alkyl, $C_{1-4}$alkoxy, $C_{1-4}$alkylenedioxy, $C_{1-4}$alkanoyl, $C_{1-4}$alkylsulphonyl, $C_{1-4}$sulphonamido, $R^7R^8N$—, —$CONR^7R^8$, $R^7R^8NSO2$—, or $R^7CON(R^8)$— group wherein each of $R^7$ and $R^8$ independently represents a hydrogen atom or a $C_{1-4}$ alkyl group, or $R^7R^8$ together form a $C_{3-6}$ alkylene chain.

Alternatively, Ar and $Ar^1$ may be optionally substituted by one or more 5- or 6-membered heterocyclic rings, as defined above, optionally substituted by a $C_{1-2}$ alkyl or $R^7R^8N$— group; wherein $R^7$ and $R^8$ are as defined above.

In the rings Ar and $Ar^1$ substituents positioned ortho to one another may be linked to form a 5- or 6-membered ring.

It will be appreciated that for use in medicine the salts of formula (I) should be physiologically acceptable. Suitable physiologically acceptable salts will be apparent to those skilled in the art and include for example acid addition salts formed with inorganic acids eg. hydrochloric, hydrobromic, sulphuric, nitric or phosphoric acid; and organic acids eg. succinic, maleic, acetic, fumaric, citric, tartaric, benzoic, p-toluenesulphonic, methanesulphonic or naphthalenesulphonic acid. Other non-physiologically acceptable salts eg. oxalates, may be used, for example in the isolation of compounds of formula (I) and are included within the scope of this invention. Also included within the scope of the invention are solvates and hydrates of compounds of formula (I).

Particular compounds according to the invention include:

(E)-7-Methoxy-2-(4-(3-phenylpropenoyl)aminobutyl)-1,2,3,4-tetrahydroisoquinoline;

(E)-7-Hydroxy-2-(4-(3-phenylpropenoyl)aminobutyl)-1,2,3,4-tetrahydroisoquinoline;

(E)-2-(4-(3-Phenylpropenoyl)aminobutyl)-7-trifluoromethylsulfonyloxy-1,2,3,4-tetrahydroisoquinoline;

(E)-2-(4-(3-(3-Nitrophenyl)propenoyl)aminobutyl)-7-trifluoromethylsulfonyloxy-1,2,3,4-tetrahydroisoquinoline;

(E)-2-(4-(3-(4-Methoxyphenyl)propenoyl)aminobutyl)-7-trifluoromethylsulfonyloxy-1,2,3,4-tetrahydroisoquinoline;

(E)-2-(4-(3-(4-Bromophenyl)propenoyl)aminobutyl)-7-trifluoromethylsulfonyloxy-1,2,3,4-tetrahydroisoquinoline;

(E)-2-(4-(3-(2-Thienyl)propenoyl)aminobutyl)-7-trifluoromethylsulfonyloxy-1,2,3,4-tetrahydroisoquinoline;

(E)-2-(4-(3-(2-Naphthyl)propenyl)aminobutyl)-7-trifluoromethylsulfonyloxy-1,2,3,4-tetrahydroisoquinoline;

(E)-2-(4-(3-(3-Furyl)propenoyl)aminobutyl)-7-trifluoromethylsulfonyloxy-1,2,3,4-tetrahydroisoquinoline;

(E)-2-(4-(3-(4-Chlorophenyl)propenoyl)aminobutyl)-7-trifluoromethylsulfonyloxy-1,2,3,4-tetrahydroisoquinoline;

(E)-2-(4-(3-(4-Dimethylaminophenyl)propenoyl)aminobutyl)-7-trifluoromethylsulfonyloxy-1,2,3,4-tetrahydroisoquinoline;

(E)-2-(4-(3-(3,4-Methylenedioxyphenyl)propenoyl)aminobutyl)-7-trifluoromethylsulfonyloxy-1,2,3,4-tetrahydroisoquinoline;

(E)-2-(4-(3-(3-(1-Methyl)indolyl)propenoyl)aminobutyl)-7-trifluoromethylsulfonyloxy-1,2,3,4-tetrahydroisoquinoline;

(E)-2-(4-(3-(1-Naphthyl)propenoyl)aminobutyl)-7-trifluoromethylsulfonyloxy-1,2,3,4-tetrahydroisoquinoline;

(E)-2-(4-(3-(2-Methylphenyl)propenoyl)aminobutyl)-7-trfluoromethylsulfonyloxy-1,2,3,4-tetrahydroisoquinoline;

(E)-2-(4-(3-(3-Cyanophenyl)propenoyl)aminobutyl)-7-trinfluoromethylsulfonyloxy-1,2,3,4-tetrahydroisoquinoline;

(E)-2-(4-(3-(2-Quinolinyl)propenoyl)aminobutyl)-7-trifluoromethylsulfonytoxy-1,2,3,4-tetrahydroisoquinoline;

(E)-2-(4-(3-(2-Methoxyphenyl)propenoyl)aminobutyl)-7-trifluoromethylsulfonyloxy-1,2,3,4-tetrahydroisoquinoline;

(E)-2-(4-(3-(3-Indolyl)propenoyl)aminobutyl)-7-trifluoromethylsulfonyloxy-1,2,3,4-tetrahydroisoquinoline;

(E)-2-(4-(3-(2-Benzofuranyl)propenoyl)amninobutyl)-7-trifluoromethylsulfonyloxy-1,2,3,4-tetrahydroisoquinoline;

(E)-2-(4-(3-(4-Acetylphenyl)propenoyl)aminobutyl)-7-trifluoromethylsulfonyloxy-1,2,3,4-tetrahydroisoquinoline;

(E)-2-(4-(3-(3-Methoxyphenyl)propenoyl)aminobutyl-7-trifluoromethylsulfonyloxy-1,2,3,4-tetrahydroisoquinoline;

(E)-2-(4-(3-(3-Quinolinyl)propenoyl)aminobutyl-7-trifluoromethylsulfonyloxy-1,2,3,4-tetrahydroisoquinoline;

(E)-2-(4-(3-(5-(2,3-Dihydro)benzofuranyl)propenoyl)aminobutyl)-7-trifluoromethylsulfonyloxy-1,2,3,4-tetrahydroisoquinoline;

(E)-2-(4-(3-(6-(1,4-benzodioxanyl))propenoyl)aminobutyl)-7-trifluoromethylsulfonyloxy-1,2,3,4-tetrahydroisoquinoline;

(E)-2-(4-(3-(3-Acetylphenyl)propenoyl)aminobutyl)-7-trifluoromethylsulfonyloxy-1,2,3,4-tetrahydroisoquinoline;

(E)-2-(4-(3-(3-Acetamidophenyl)propenoyl)aminobutyl)-7-trifluoromethylsulfonyloxy-1,2,3,4-tetrahydroisoquinoline;

(E)-2-(4-(3-(3-Dimethylaminophenyl)propenoyl)aminobutyl)-7-trifluoromethylsulfonyloxy-1,2,3,4-tetrahydroisoquinoline;

(E)-2-(4-(3-(2-Quinoxalinyl)propenoyl)aminobutyl)-7-trifluoromethylsulfonyloxy-1,2,3,4-tetrahydroisoquinoline;

(E)-2-(4-(3-(2-Benzothiazolyl)propenoyl)aminobutyl)-7-trifluoromethylsulfonyloxy-1,2,3,4-tetrahydroisoquinoline;

(E)-2-(4-(3-(3,4-Dichlorophenyl)propenoyl)aminobutyl)-7-trifluoromethylsulfonyioxy-1,2,3,4-tetrahydroisoquinoline;

(E)-2-(4-(3-(2-(1-Methyl)pyrrolyl)propenoyl)aminobutyl)-7-trifluoromethylsulfonyloxy-1,2,3,4-tetrahydroisoquinoline;

(E)-2-(4-(3-(5-Pyrido[2,3-b]indolyl)propenoyl)aminobutyl-7-trifluoromethylsulfonyloxy-1,2,3,4-tetrahydroisoquinoline;

(E)-2-(4-(3-(5-(2-Dimethylamino)pyrimidyl)propenoyl)aminobutyl)-7-trifluoromethylsulfonyloxy-1,2,3,4-tetrahydroisoquinoline;

(E)-2-(4-(3-(2-Benzoxazolyl)propenoyl)aminobutyl)-7-trifluoromethylsulfonyloxy-1,2,3,4-tetrahydroisoquinoline;

(E)-2-(4-(3-(4-(1-Pyrrolidinyl)phenyl)propenoyl)aminobutyl)-7-trifluoromethylsulfonyloxy-1,2,3,4-tetrahydroisoquinoline;

(E)-2-(4-(3-(3-Methylaminocarbonylphenyl)propenoyl)aminobutyl)-7-trifluoromethylsulfonyloxy-1,2,3,4-tetrahydroisoquinoline;

(E)-2-(4-(3-(3,4-Methylenedioxyphenyl)propenoyl)aminobutyl)-7-trifluoromethylsulfonyloxy-1,2,3,4-tetrahydroisoquinoline;

(E)-2-(4-(3-(3-Aminocarbonylphenyl)propenoyl)aminobutyl)-7-trifluoromethylsulfonyloxy-1,2,3,4-tetrahydroisoquinoline;

(E)-2-(4-(3-(2-Acetamidophenyl)propenoyl)aminobutyl)-7-trifluoromethylsulfonyloxy-1,2,3,4-tetrahydroisoquinoline;

(E)-2-(4-(3-(2-Naphthyl)propenoyl)aminobutyl)-7-(2-thiophene)sulfonyloxy-1,2,3,4-tetrahydroisoquinoline;

(E)-2-(4-(3-(4-Dimethylaminophenyl)propenoyl)aminobutyl)-7-(2-thiophene)sulfonyloxy-1,2,3,4-tetrahydroisoquinoline;

(E)-2-(4-(3-(2-Naphthyl)propenoyl)aminobutyl-7-methylsulfonyloxy-1,2,3,4-tetrahydroisoquinoline;

(E)-2-(4-(3-(4-Dimethylaminophenyl)propenoyl)aminobutyl)-7-methylsulfonyloxy-1,2,3,4-tetrahydroisoquinoline;

(E)-2-(4-(3-(2-Naphthyl)propenoyl)aminobutyl)-7-acetyl-1,2,3,4-tetrahydroisoquinoline;

(E)-2-(4-(3-(2-Naphthyl)propenoyl)aminobutyl)-7-bromo-1,2,3,4-tetrahydroisoquinoline;

(E)-2-(4-(3-(2-Naphthyl)propenoyl)aminobutyl)-7-(4-cyanophenyl)sulfonyloxy-1,2,3,4-tetrahydroisoquinoline;

(E)-2-(4-(3-(2-Naphthyl)propenoyl)aminobutyl)-7-methoxy-1,2,3,4-tetrahydroisoquinoline;

(E)-7-Phenylsulfonylmethyl-2-(4-(3-(2-naphthyl)propenoyl)aminobutyl)-1,2,3,4-tetrahydroisoquinoline;

(E)-7-Methylsulfonamido-2-(4-(3-(2-naphthyl)propenyl)aminobutyl)-1,2,3,4-tetrahydroisoquinoline;

(E)-2-(4-(3-(2-Naphthyl)propenoyl)aminobutyl)-7-phenylsulfonamido-1,2,3,4-tetrahydroisoquinoline;

(E)-7-(4-Cyanophenyl)sulfonamido-2-(4-(3-(2-naphthyl)propenoyl)aminobutyl-1,2,3,4-tetrahydroisoquinoline;

(E)-2-(4-(3-(5-Indolyl)propenoyl)aminobutyl)-7-trifluoromethylsulfonyloxy-1,2,3,4-tetrahydroisoquinoline;

(E)-2-(4-(3-(5-Benzimidazolyl)propenoyl)aminobutyl)-7-trifluoromethylsulfonyloxy-1,2,3,4-tetrahydroisoquinoline;

(E)-7-Methylsulfonylmethyl-2-(4-(3-(2-naphthyl)propenoyl)aminobutyl)-1,2,3,4-tetrahydroisoquinoline;

(E)-2-(4-(3-(2-Naphthyl)propenoyl)aminobutyl)-7-trifluoromethoxy-1,2,3,4-tetrahydroisoquinoline;

(E)-7-Cyano-2-(4-(3-(2-naphthyl)propenoyl)aminobutyl)-1,2,3,4-tetrahydroisoquinoline;

(E)-2-(4-(3-(3-Indolyl)propenoyl)aminobutyl)-7-trifluoromethoxy-1,2,3,4-tetrahydroisoquinoline;

(E)-2-(4-(3-(4-Dimethylaminophenyl)propenoyl)-7-trifluoromethoxy-1,2,3,4-tetrahydroisoquinoline;

(E)-2-(4-(3-(4-Aminophenyl)propenoyl)aminobutyl)-7-trifluoromethylsulfonyloxy-1,2,3,4-tetrahydroisoquinoline;

(E)-2-(4-(3-(4-Nicrophenyl)propenoyl)aminobutyl)-7-trifluoromethylsulfonyloxy-1,2,3,4-tetrahydroisoquinoline;

(E)-7-Cyano-2-(4-(3-(3-indolyl)propenoyl)aminobutyl)-1,2,3,4-tetrahydroisoquinoline;

(E)-2-(4-(3-(7-(Methyl)indolyl)propenoyl)aminobutyl)-7-trifluoromethylsulfonyloxy-1,2,3,4-tetrahydroisoquinoline;

(E)-2-(4-(3-(2-(6-Acetyl)naphthyl)propenoyl)aminobutyl)-7-trifluoromethylsulfonyloxy-1,2,3,4-tetrahydroisoquinoline;

(E)-7-Cyano-2-(4-(3-(3-(7-methyl)indolyl)propenoyl)aminobutyl)-1,2,3,4-tetrahydroisoquinoline;

(E)-7-Cyano-2-(4-(3-(5-benzimidazolyl)propenoyl)aminobutyl)-1,2,3,4-tetrahydroisoquinoline;

(E)-7-Cyano-2-(4-(3-(5-indolyl)propenoyl)aminobutyl)-1,2,3,4-tetrahydroisoquinoline;

(E)-2-(4-(3-(2-(6-Acetyl)naphthyl)propenoyl)aminobutyl)-7-cyano-1,2,3,4-tetrahydroisoquinoline;

(E)-7-Cyano-2-(4-(3-(6-indolyl)propenoyl)aminobutyl)-1,2,3,4-tetrahydroisoquinoline;

(E)-7-Cyano-2-(4-(3-(3-(7-fluoro)indolyl)propenoyl)aminobutyl)-1,2,3,4-tetrahydroisoquinoline;

(E)-2-(4-(3-(3-(7-Bromo)indolyl)propenoyl)aminobutyl)-7-trifluoromethoxy-1,2,3,4-tetrahydroisoquinoline;

(E)-2-(4-(3-(3-(7-Bromo)indolyl)propenoyl)aminobutyl)-7-cyano-1,2,3,4-tetrahydroisoquinoline;

(E)-2-(4-(3-(3-(7-Cyano)indolyl)propenoyl)aminobutyl)-7-cyano-1,2,3,4-tetrahydroisoquinoline;

(E)-7-Cyano-2-(4-(3-(5-(2-methyl)indolyl)propenoyl)aminobutyl)-1,2,3,4-tetrahydroisoquinoline;

(E)-2-(4-(3-(5-(2-Methyl)indolyl)propenoyl)aminobutyl)-7-trifluoromethoxy-1,2,3,4-tetrahydroisoquinoline;

(E)-2-(4-(3-(3-(7-Acetyl)indolyl)propenoyl)aminobutyl)-7-cyano-1,2,3,4-tetrahydroisoquinoline;

(E)-7-Cyano-2-(4-(3-(6-(2-methyl)indolyl)propenoyl)aminobutyl)-1,2,3,4-tetrahydroisoquinoline;

(E)-7-Cyano-2-(4-(3-(5-(2,3-dihydro-2-oxo)-1H-indolyl)propenoyl)aminobutyl)-1,2,3,4-tetrahydroisoquinoline;

(E)-2-(4-(3-(6-(1,2-Dihydro-2-oxo)quinolinyl)propenoyl)aminobutyl)-7-trifluoromethoxy-1,2,3,4-tetrahydroisoquinoline;

(E)-2-(4-(3-(5-(2-Acetyl)indolyl)propenoyl)aminobutyl)-7-cyano-1,2,3,4-tetrahydroisoquinoline;

(E)-7-Chloro-2-(4-(3-(6-indolyl)propenoyl)aminobutyl)-1,2,3,4-tetrahydroisoquinoline;

(E)-7-Cyano-2-(4-(3-(5-(3-methyl)indolyl)propenyl)aminobutyl)-1,2,3,4-tetrahydroisoquinoline;

(E)-2-(4-(3-(6-(3-Methyl)indolyl)propenoyl)aminobutyl)-7-trifluoromethoxy-1,2,3,4-tetrahydroisoquinoline;

(E)-7-Cyano-2-(4-(3-(5-(1-methyl)indolyl)propenoyl)aminobutyl)-1,2,3,4-tetrahydroisoquinoline;

(E)-2-(4-(3-(2-(1-Methyl)indolyl)propenoyl)aminobutyl)-7-trifluoromethylsulfonyloxy-1,2,3,4-tetrahydroisoquinoline;

(E)-2-(4-(3-(5-Indolyl)propenoyl)aminobutyl)-1,2,3,4-tetrahydroisoquinoline;

(E)-7-Cyano-2-(4-(3-(5-(2-methyl)benzimidazolyl)propenoyl)aminobutyl)-1,2,3,4-tetrahydroisoquinoline;

(E)-2-(4-(3-(5-(2-Methyl)benzimidazolyl)propenoyl)aminobutyl)-7-trifluoromethoxy-1,2,3,4-tetrahydroisoquinoline;

(E)-2-(4-(3-(5-Indolyl)propenoyl)aminobutyl)-7-trifluoromethyl-1,2,3,4-tetrahydroisoquinoline;

(E)-2-(4-(3-(5-Indolyl)propenoyl)aminobutyl)-7-methylsulfonamido-1,2,3,4-tetrahydroisoquinoline;

(E)-2-(4-(3-(5-Indolyl)propenoyl)aminobutyl)-7-methylaminosulfonyl-1,2,3,4-tetrahydroisoquinoline;

(E)-2-(4-(3-(3-(7-Methyl)indolyl)propenoyl)aminobutyl)-7-trifluoromethoxy-1,2,3,4-tetrahydroisoquinoline;

(E)-7-Cyano-2-(4-(3-(5-(3-dimethylaminomethyl) indolyl)propenoyl)aminobutyl)-1,2,3,4-tetrahydroisquinoline;
and salts thereof.

The present invention also provides a process for preparing compounds of formula (I) which process comprises:

(a) reacting a compound of formula (II):

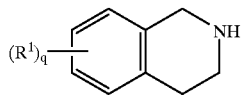

Formula (II)

wherein $R^1$ and q are as hereinbefore defined;
with a compound of formula (III):

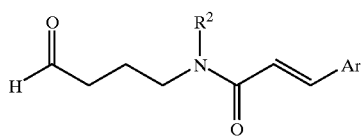

Formula (III)

wherein $R^2$ and Ar are as hereinbefore defined;

(b) reaction of a compound of formula (IV):

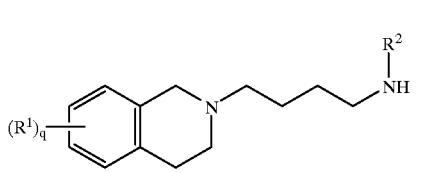

Formula (IV)

wherein $R^1$ and $R^2$ are as hereinbefore defined;
with a compound of formula (V):

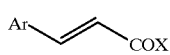

Formula (V)

wherein Ar is as hereinbefore defined and X is a halogen atom or the residue of an activated ester;

(c) to prepare a compound of formula (I) wherein $R^1$ is $Ar^1$—Z and Z is a bond, reacting a compound of formula (VI):

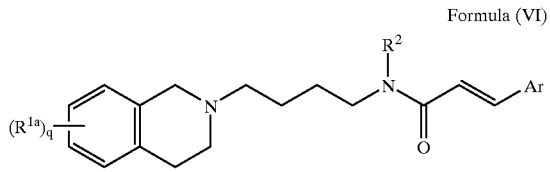

Formula (VI)

wherein one $R^{1a}$ represents a group W wherein W is a halogen atom or a trifluoromethylsulphonyloxy group, or W is a group M selected from a boron derivative e.g. a boronic acid function $B(OH)_2$ or a metal function such as trialkylstannyl e.g. $SnBu_3$, zinc halide or magnesium halide, and when q is 2 the other $R^{1a}$ is $R^1$; with a compound $Ar^1$—$W^1$, wherein $W^1$ is a halogen atom or a trifluoromethylsulphonyloxy group when W is a group M or $W^1$ is a group M when W is a halogen atom or a trifluoromethylsulphonyloxy group;

(d) to prepare a compound of formula (I) wherein $R^1$ is $Ar^1$—Z and Z is O or S, reacting a compound of formula (VII):

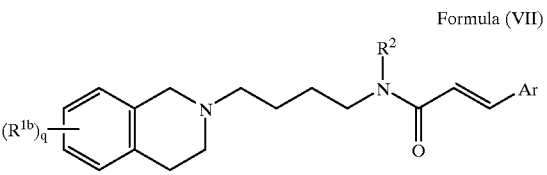

Formula (VII)

wherein one $R^{1b}$ represent a group ZH and when q is 2 the other $R^{1b}$ represents $R^1$; with a reagent serving to introduce the group $Ar^1$;

(e) interconversion of one compound of formula (I) to a different compound of formula (I) e.g. (i) alkylation of a compound (I) wherein $R^2$ represents hydrogen, (ii) conversion of one $R^1$ from alkoxy (e.g.methoxy) to hydroxy, or (iii) conversion of $R^1$ from hydroxy to sulphonyloxy, eg alkylsulphonyloxy or trifluoromethanesulphonyloxy; and optionally thereafter forming a salt of formula (I).

Process (a) requires the presence of a reducing agent. Suitable reducing agents which may be employed include sodium borohydride, cyanoborohydride or triacetoxyborohydride under acidic conditions, or catalytic hydrogenation. The reaction may conveniently be effected in a solvent such as ethanol.

Process (b) may be effected by methods well known in the art for formation of an amide bond.

Reaction of a compound of formula (VI) with $Ar^1W^1$, according to process (c) may be effected in the presence of a transition metal eg palladium catalyst such as bis-triphenylphosphinepalladium dichloride or tetrakis-triphenylphosphinepalladium (0). When M represents a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. The substituent W is preferably a halogen atom such as bromine, or a sulphonyloxy group such as trifluoromethylsulphonyloxy; and $W^1$ is preferably a group M, such as trialkylstannyl or $B(OH)_2$.

In process (d) the reagent serving to introduce the group $Ar^1$ is preferably a compound of formula $Ar^1$—Hal, wherein Hal is a halogen atom. The reaction may be effected in the presence of a base, such as potassium carbonate, in a solvent such as dimethylformamide.

Interconversion reactions according to process (e) may be effected using methods well known in the art.

Compounds of formula (II) may be prepared by methods known in the art.

Compounds of formula (III) are known or may be prepared using standard procedures.

A compound of formula (IV) may be prepared by alkylation of a compound (II) by standard methods. Thus, for example a compound of formula (II) may be reacted with N-(4-bromobutylphthalimide) followed by removal of the phthalimide group to give a compound of formula (IV) where $R^2$ is hydrogen. Compounds where $R^2$ is alkyl may be prepared by subsequent reaction with the appropriate aldehyde using conditions analogous to process (a) above.

Compounds of formula (VI), and (VII) may be prepared by processes analogous to (a) or (b) described above.

Compounds Ar$^1$W$^1$ and Ar$^1$Hal are commercially available or may be prepared by standard methods.

Compounds of formula (I) have been found to exhibit affinity for dopamine receptors, in particular the D$_3$ receptor, and are expected to be useful in the treatment of disease states which require modulation of such receptors, such as psychotic conditions. Compounds of formula (I) have also been found to have greater affinity for dopamine D$_3$ than for D$_2$ receptors. The therapeutic effect of currently available antipsychotic agents (neuroleptics) is generally believed to be exerted via blockade of D$_2$ receptors; however this mechanism is also thought to be responsible for undesirable extrapyramidal side effects (eps) associated with many neuroleptic agents. Without wishing to be bound by theory, it has been suggested that blockade of the recently characterised dopamine D$_3$ receptor may give rise to beneficial antipsychotic activity without significant eps. (see for example Sokoloff et al, Nature, 1990; 347: 146–151; and Schwartz et al, Clinical Neuropharmacology, Vol 16, No. 4, 295–314, 1993). Preferred compounds of the present invention are therefore those which have higher affinity for dopamine D$_3$ than dopamine D$_2$ receptors (such affinity can be measured using standard methodology for example using cloned dopamine receptors). Said compounds may advantageously be used as selective modulators of D$_3$ receptors.

We have found that certain compounds of formula (I) are dopamine D$_3$ receptor antagonists, others may be agonists or partial agonists. The functional activity of compounds of the invention (i.e. whether they are antagonists, agonists or partial agonists) can be readily determined using the test method described hereinafter, which does not require undue experimentation. D$_3$ antagonists are of potential use as antipsychotic agents for example in the treatment of schizophrenia, schizo-affective disorders, psychotic depression and mania. Conditions which may be treated by dopamine D$_3$ receptor agonists include dyskinetic disorders such as Parkinson's disease, neuroleptic-induced parkinsonism and tardive dyskinesias; depression; anxiety, memory disorders, sexual dysfunction and drug (eg. cocaine) dependency.

In a further aspect therefore the present invention provides a method of treating conditions which require modulation of dopamine D$_3$ receptors, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine D$_3$ receptors, for example psychoses such as schizophrenia.

A preferred use for D$_3$ antagonists according to the present invention is in the treatment of psychoses such as schizophrenia.

A preferred use for D$_3$ agonists according to the present invention is in the treatment of dyskinetic disorders such as Parkinson's disease.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

Biological Test Methods

The ability of the compounds to bind selectively to human $D_3$ dopamine receptors can be demonstrated by measuring their binding to cloned receptors. The inhibition constants ($K_i$) of test compounds for displacement of [$^{125}$I] iodosulpride binding to human $D_3$ dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −40° C. Crude cell membranes were prepared by homogenisation followed by high-speed centrifugation, and characterisation of cloned receptors achieved by radioligand binding.

Preparation of CHO Cell Membranes

Cell pellets were gently thawed at room temperature, and resuspended in about 20 volumes of ice-cold 50 mM Tris salts (pH 7.4 @ 37° C.), 20 mM EDTA, 0.2 M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4 @ 37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4 @ 37° C.). The final pellet was resuspended in 50 mM Tris salts (pH 7.4 @ 37° C.), and the protein content determined using bovine serum albumin as a standard (Bradford, M. M. (1976) Anal. Biochem. 72, 248–254).

Binding Experiments on Cloned Dopamine Receptors

Crude cell membranes were incubated with 0.1 nM [$^{125}$I] iodosulpride (~2000 Ci/mmol; Amersham, U. K.), and the test compound in a buffer containing 50 mM Tris salts (pH 7.4 @ 37° C.), 120 mM NaCl, 5 mM KCl, 2 mM $CaCl_2$, 1 mM $MgCl_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4 @ 37° C.), 120 mM NaCl, 5 mM KCl, 2 mM $CaCl_2$, 1 mM $MgCl_2$. The radioactivity on the filters was measured using a Cobra gamma counter (Canberra Packard). Non-specific binding was defined as the radioligand binding remaining after incubation in the presence of 100 μM iodosulpride. For competition curves, 14 concentrations (half-log dilutions) of competing cold drug were used.

Competition curves were analysed simultaneously whenever possible using non-linear least-squares fitting procedures, capable of fitting one, two or three site models.

Compounds of Examples had pKi values of between 7.0 and 9.0 at the dopamine $D_3$ receptor.

Functional Activity at Cloned Dopamine Receptors

The functional activity of compounds at human D2 and human D3 receptors (ie agonism or antagonism) may be determined using a Cytosensor Microphysiometer (McConnell HM et al Science 1992 257 1906–1912). In Microphysiometer experiments, cells (hD2_CHO or hD3_CHO) were seeded into 12 mm Transwell inserts (Costar) at 300000 cells/cup in foetal calf serum (FCS)-containing medium. The cells were incubated for 6 h at 37° C. in 5% $CO_2$, before changing to FCS-free medium. After a further 16–18 h, cups were loaded into the sensor chambers of the Cytosensor Microphysiometer (Molecular Devices) and the chambers perfused with running medium (bicarbonate-free Dulbecco's modified Eagles medium containing 2 mM glutamine and 44 mM NaCl) at a flow rate of 100 μl/min. Each pump cycle lasted 90s. The pump was on for the first 60s and the acidification rate determined between 68 and 88s, using the Cytosoft programme. Agonists and antagonists were diluted in running medium. In experiments to determine agonist activity, cells were exposed (4.5 min for hD2, 7.5 min for hD3) to increasing concentrations of putative agonist at half hour intervals. Seven concentrations of agonist were used. Peak acidification rate to each agonist concentration was determined and concentration-response curves fitted using Robofit [Tilford, N. S., Bowen, W. P. & Baxter, G. S. Br. J. Pharmacol. (1995) in press]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

Pharmaceutical Formulations

The following represent typical pharmaceutical formulations according to the present invention, which may be prepared using standard methods.

| IV Infusion | |
|---|---|
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |

Buffer: Suitable buffers include citrate, phosphate, sodium hydroxide/hydrochloric acid.

Solvent: Typically water but may also include cyclodextrins (1–100 mg) and co-solvents such as propylene glycol, polyethylene glycol and alcohol.

| Tablet | |
|---|---|
| Compound | 1–40 mg |
| Diluent/Filler* | 50–250 mg |
| Binder | 5–25 mg |
| Disentegrant* | 5–50 mg |
| Lubricant | 1–5 mg |
| Cyclodextrin | 1–100 mg |

Tablet

*may also include cyclodextrins

Diluent: e.g. Microcrystalline cellulose, lactose, starch

Binder: e.g. Polyvinylpyrrolidone, hydroxypropymethylcellulose

Disintegrant: e.g. Sodium starch glycollate, crospovidone

Lubricant: e.g. Magnesium stearate, sodium stearyl fumarate.

| Oral Suspension | |
| --- | --- |
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent: e.g. Xanthan gum, microcrystalline cellulose

Diluent: e.g. sorbitol solution, typically water

Preservative: e.g. sodium benzoate

Buffer: e.g. citrate

Co-solvent: e.g. alcohol, propylene glycol, polyethylene glycol, cyclodextrin

The invention is further illustrated by the following non-limiting examples:

Description 1
4-Phthalimidobutyraldehyde Diethyl Acetal

A solution of 4-aminobutyraldehyde diethyl acetal (48.5 g, 0.3 mol) in tetrahydrofuran (60 ml) was added dropwise to a stirred slurry of N-(ethoxycarbonyl) phthalimide (65.93 g, 0.3 mol) in tetrahydrofuran (250 ml) at 0° C. After stirring at 0° C. for 0.16 h and at room temperature for 18 h the solvent was removed in vacuo and the residue distilled at 1 mmHg to remove the ethyl carbamate by-product. The residual brown oil was allowed to cool to afford the title compound (91 g, 93%).

Mass spectrum (API$^+$): 218 (MH$^+$ for aldehyde). $^1$H NMR (CDCl$_3$) δ: 1.20 (6H, t, J=7 Hz), 1.70 (4H, m), 3.35–3.85 (6H, m), 4.55 (1H, t, J=5 Hz), 7.70 (2H, m), 7.85 (2H, m).

Description 2
4-Phthalimidobutyraldehyde

A solution of 4-phthalimidobutyraldehyde diethyl acetal (125 g, 0.43 mol) in a 1:1 mixture of tetrahydrofuran and 2N hydrochloric acid (800 ml) was heated at reflux for 0.75 h. The mixture was cooled, concentrated to 400 ml and extracted into dichloromethane (3×200 ml). Combined organics were dried (Na$_2$SO$_4$) and evaporated in vacuo to afford the title compound as a brown oil that solidified on standing (95 g, 100%).

Mass spectrum (API$^+$): 218 (MH$^+$), C$_{12}$H$_{11}$NO$_3$ requires 217. $^1$H NMR (CDCl$_3$) δ: 2.00 (2H, m), 2.55 (2H, t, J=5 Hz), 3.75 (2H, t, J=5 Hz), 7.70 (2H, m), 7.85 (2H, m), 9.30 (1H, s).

Description 3
7-Methoxy-2-(4-phthalimidobutyl)-1,2,3,4-tetrahydroisoquinoline To a stirred solution of 4-phthalimidobutyraldehyde (15.96 g, 0.074 mol) and 7-methoxy-1,2,3,4-tetrahydroisoquinoline (10 g, 0.061 mol) in 1,2-dichloroethane (100 ml) was added sodium triacetoxyborohydride (19.3 g, 0.091 mol) in three equal portions over 10 mins, followed by glacial acetic acid (3.72 ml, 0.061 mol). The resultant mixture was stirred at room temperature for 3 h, then at 45° C. for 1 h, and poured into saturated aqueous potassium carbonate (600 ml). The mixture was extracted into dichloromethane (2×400 ml) and the combined extracts dried (Na$_2$SO$_4$) and evaporated in vacuo. Trituration of the residue with hexane afforded the title compound as a pale brown gum (13.5 g, 60%).

Mass spectrum (API$^+$): 365 (MH$^+$) C$_{22}$H$_{24}$N$_2$O$_3$ requires 364. $^1$H NMR (CDCl$_3$) δ: 1.70 (4H, m), 2.50 (2H, m), 2.70 (2H, m), 2.80 (2H, m), 3.55 (2H, s), 3.55–3.80 (5H, m), 6.55 (1H, d, J=2 Hz), 6.70 (1H, dd, J=2 Hz, 8 Hz), 7.00 (1H, d, J=8 Hz), 7.70 (2H, m), 7.85 (2H, m).

The following compounds were prepared in a similar manner to Description 3:

(a) 7-Nitro-2-(4-phthalimidobutyl)-1,2,3,4-tetrahydroisoquinoline

Mass spectrum (API$^+$): Found 380 (MH$^+$). C$_{21}$H$_{21}$N$_3$O$_4$ requires 379.

(b) 7-Bromo-2-(4-phthalimidobutyl)-1,2,3,4-tetrahydroisoquinoline

Mass spectrum (API$^+$): Found 413 (MH$^+$). C$_{21}$H$_{21}$$^{79}$BrN$_2$O$_2$ requires 412.

(c) 7-Phenylsulfonylmethyl-2-(4-phthalimidobutyl)-1,2,3,4-tetrahydroisoquinoline Mass spectrum (API$^+$): Found 489 (MH$^+$). C$_{28}$H$_{28}$N$_2$O$_4$S requires 488.

(d) 7-Methylsulfonylmethyl-2-(4-phthalimidobutyl)-1,2,3,4-tetrahydroisoquinoline Mass spectrum (API$^+$): Found 427 (MH$^+$). C$_{23}$H$_{26}$N$_2$O$_4$S requires 426.

(e) 2-(4-Phthalimidobutyl)-7-trifluoromethoxy-1,2,3,4-tetrahydroisoquinoline

Mass spectrum (API$^+$): Found 419 (MH$^+$). C$_{22}$H$_{21}$F$_3$N$_2$O$_3$ requires 418.

Description 4
2-(4-Aminobutyl)-7-methoxy-1,2,3,4-tetrahydroisoquinoline

A solution of 7-methoxy-2-(4-phthalimidobutyl)-1,2,3,4-tetrahydroisoquinoline (17.4 g 0.0478 mol) and hydrazine monohydrate (4.6 ml, 0.095 mol) in ethanol (300 ml) were stirred at room temperature for 18 h and at reflux for 1 h. The cooled reaction mixture was filtered and the filtrate evaporated in vacuo. The residue was dissolved in 2.5N hydrochloric acid, filtered through Kieselguhr and the filtrate basified with 0.880 ammonia. The product was extracted into dichloromethane (4×200 ml), the combined extracts were dried (Na$_2$SO$_4$) and evaporated in vacuo to afford the title compound as a brown oil (7 g, 63%).

Mass spectrum (API$^+$): 235 (MH$^+$) C$_{14}$H$_{22}$N$_2$O requires 234. $^1$H NMR (CDCl$_3$) δ: 1.30–1.90 (4H, m), 2.50 (2H, m), 2.60–2.90 (8H, m), 3.60 (2H, s), 3.75 (3H, s), 6.55 (1H, d, J=2 Hz), 6.70 (1H, dd, J=2 Hz, 8 Hz), 7.00 (1H, d, J=8 Hz).

Description 5
7-Hydroxy-2-(4-phthalimidobutyl)-1,2,3,4-tetrahydroisoquinoline Prepared from 7-methoxy-2-(4-phthalimidobutyl)-1,2,3,4-tetrahydroisoquinoline (1.45 g, 3.98 mmol) using a procedure similar to that of Example 2 (1.31 g, 94%).

Mass spectrum (API$^+$): 351 (MH$^{30}$) C$_{21}$H$_{22}$N$_2$O$_3$ requires 350. $^1$H NMR (CDCl$_3$) δ: 1.70 (4H, m), 2.25–2.85 (1H, br s), 2.50 (2H, t, J=7 Hz), 2.70 (2H, d, J=4 Hz), 2.85 (2H, d, J=4 Hz), 3.50 (2H, s), 3.75(2H, t, J=7 Hz), 6.45 (1H, d, J=2 Hz), 6.60 (1H,dd, J=2 Hz, 8 Hz), 6.90 (1H, d, J=8 Hz), 7.70 (2H, m), 7.85 (2H, m).

Description 6

2-(4-Phthalimidobutyl)-7-trifluoromethylsulfonyloxy 1,2,3,4-tetrahydroisoquinoline Trifluoromethanesulfonic anhydride (0.53 ml, 3.14 mmol) was added dropwise with stirring to an ice-cooled solution of 7-hydroxy-2-(4-phthalimidobutyl)-1,2,3,4-tetrahydroisoquinoline (1 g, 2.86 mmol) in anhydrous pyridine (10 ml). After stirring at room temperature for 18 h the reaction mixture was added to 10% aqueous Copper (II) sulfate (100 ml) and extracted into ethyl acetate (200 ml). The organic layer was separated, washed with 10% aqueous copper (II) sulfate (2×50 ml), dried (Na$_2$SO$_4$) and evaporated in vacuo. Chromatography on silica gel using 10–100% ethyl acetate-hexane gradient elution gave the title compound as a green oil (0.45 g, 33%).

Mass spectrum (API$^+$): 483 (MH$^+$). C$_{22}$H$_{21}$F$_3$N$_2$O$_5$S requires 482. $^1$H NMR (CDCl$_3$) δ: 1.75 (4H, m), 2.55 (2H, t, J=7 Hz), 2.75 (2H, t, J=6 Hz), 2.90 (2H, t, J=6 Hz), 3.60 (2H, s), 3.75 (2H, t, J=7 Hz), 6.90 (1H, d, J=2 Hz), 7.05 (1H, dd, J=2 Hz, 9 Hz), 7.15 (1H, d, J=9 Hz), 7.70 (2H, m), 7.85 (2H, m).

Description 7

2-(4-Aminobutyl)-7-trifluoromethylsulfonyloxy-1,2,3,4-tetrahydroisoquinoline

Prepared from 2-(4-phthalimidobutyl)-7-trifluoromethylsulfonyloxy-1,2,3,4-tetrahydroisoquinoline (0.44 g, 0.91 mmol) using a procedure similar to that of Description 4 (0.26 g, 81%).

Mass spectrum (API$^+$): 353 (MH$^+$). C$_{14}$H$_{19}$F$_3$N$_2$O$_3$S requires 352. $^1$H NMR (CDCl$_3$) δ: 1.50 (6H, m), 2.50 (2H, t, J=7 Hz), 2.75 (4H, m), 2.90 (2H, t, J=6 Hz), 3.60 (2H, s), 6.90 (1H, d, J=2 Hz), 7.0 (1H, dd, J=2 Hz, 9 Hz), 7.15 (1H, d, J=9 Hz).

The following compounds were prepared in a similar manner to Description 7:

(a) 2-(4-Aminobutyl)-7-methylsulfonamido-1,2,3,4-tetrahydroisoquinoline $^1$H NMR (CDCl$_3$) δ: 1.36 (4H, m), 2.50 (2H, m), 2.70 (4H, m), 2.82 (2H, m), 2.91 (3H, s), 3.39 (3H, m), 3.54 (2H, s), 6.85 (1H, d, J=2 Hz), 6.89–7.06 (2H, m).

(b) 2-(4-Aminobutyl)-7-phenylsulfonamido-1,2,3,4-tetrahydroisoquinoline $^1$H NMR (CDCl$_3$) δ: 1.39 (4H, m), 2.09 (2H, br s), 2.48 (2H, t, J=7 Hz), 2.60–2.92 (6H, m), 3.50 (2H, s), 6,76 (2H, m), 6.95 (1H, d, J=8 Hz), 7.37–7.62 (4H, m), 7.73 (2H, m).

(c) 2-(4-Aminobutyl)-7-(4-cyanophenyl)sulfonamido-1,2,3,4-tetrahydroisoquinoline Mass spectrum (API$^+$): Found 385 (MH$^+$). C$_{20}$H$_{24}$N$_4$O$_2$S requires 384.

(d) 2-(4-Aminobutyl)-7-bromo-1,2,3,4-tetrahydroisoquinoline $^1$H NMR (CDCl$_3$) δ: 1.30–1.67 (6H, m), 2.48 (2H, d, J=7 Hz), 2.60–2.87 (6H, m), 3.55 (2H, s), 6.94 (1H, d, J=9 Hz), 7.15 (1H, d, J=2 Hz), 7.23 (1H, d, J=9, 2 Hz).

(e) 2-(4-Aminobutyl)-7-methylsulfonyloxy-1,2,3,4-tetrahydroisoquinoline

Mass spectrum (API$^+$): Found 299 (MH$^+$). C$_{14}$H$_{22}$N$_2$O$_3$S requires 298.

(f) 2-(4-Aminobutyl)-7-(2-thiophenesulfonyloxy)-1,2,3,4-tetrahydroisoquinoline

Mass spectrum (API$^+$): Found 367 (MH$^+$). C$_{17}$H$_{22}$N$_2$O$_3$S$_2$ requires 366.

(g) 2-(4-Aminobutyl)-7-(4-cyanophenylsulfonyloxy)-1,2,3,4-tetrahydroisoquinoline Mass spectrum (API$^+$): Found 386 (MH$^+$). C$_{20}$H$_{23}$N$_3$O$_3$S requires 385.

(h) 2-(4-Aminobutyl)-7-phenylsulfonylmethyl-1,2,3,4-tetrahydroisoquinoline

Mass spectrum (API$^+$): Found 359 (MH$^+$). C$_{20}$H$_{26}$N$_2$O$_2$S requires 358.

(i) 2-(4-Aminobutyl)-7-Methylsulfonylmethyl-1,2,3,4-tetrahydroisoquinoline

Mass spectrum (API$^+$): Found 297 (MH$^+$). C$_{15}$H$_{24}$N$_2$O$_2$S requires 296.

(j) 2-(4-Aminobutyl)-7-trifluoromethoxy-1,2,3,4-tetrahydroisoquinoline

Mass spectrum (API$^+$): Found 289 (MH$^+$). C$_{14}$H$_{19}$F$_3$N$_2$O requires 288.

Description 8

(E)-3-(5-(2-Dimethylamino)pyrimidyl)propenoic Acid, Methyl Ester

A solution of (2-dimethylamino)pyrimidine-5-carboxaldehyde [Gupton J. T. et al, J. Het. Chem 28, 1281–5 (1991)] (250 mg, 1.66 mmol) and carbomethoxymethylenetriphenyl phosphorane (554 mg, 1.66 mmol) in chloroform (100 ml) was refluxed for 2 h. The reaction mixture was concentrated to 10 ml and chromatographed on a silica column topped with neutral alumina using 10–30% ethyl acetate-hexane gradient elution to afford the title compound (280 mg, 82%).

$^1$H NMR (CDCl$_3$) δ: 3.25 (6H, s), 3.80 (3H, s), 6.25 (1H, d, J=15 Hz), 7.50 (1H, d, J=15 Hz), 8.50 (2H, s).

The following compounds were prepared in a similar manner to Description 8:

(a) (E)-3-(4-(1-Pyrrolidinyl)phenyl)propenoic acid, methyl ester $^1$H NMR (CDCl$_3$) δ: 2.00 (4H, m), 3.30 (4H, m), 3.80 (3H, s), 6.20 (1H, d, J=15 Hz), 6.50 (2H, d, J=8 Hz), 7.40 (2H, d, J=8 Hz), 7.65 (1H, d, J=15 Hz).

(b) (E)-3-(5-(2,3-Dihydro)benzofuranyl)propenoic acid, methyl ester

Mass spectrum (API$^+$): Found 205 (MH$^+$). C$_{12}$H$_{12}$O$_3$ requires 204.

Description 9

(E)-3-(5-(2-Dimethylamino)pyrimidyl)propenoic Acid

A mixture of (E)-3-(5-(2-dimethylamino)pyrimidyl)propenoic acid, methyl ester (250 mg, 1.2 mmol) and sodium hydroxide (98 mg, 2.45 mmol) in water (30 ml) was heated at reflux for 3 h. The resultant solution was cooled, washed with ethyl acetate (50 ml) and adjusted to pH6 with 5N HCl. The resultant precipitate was filtered, washed with water and dried in vacuo (195 mg, 84%).

$^1$H NMR (DMSO) δ: 3.20 (6H, s), 6.40 (1H, d, J=15 Hz), 7.45 (1H, d, J=15 Hz), 8.70 (2H, s), 12.25 (1H, br s).

The following compounds were prepared in a similar manner to Description 9:

(a) (E)-3-(4-(1-Pyrrolidinyl)phenyl)propenoic acid

Mass spectrum (API$^+$): Found 216 (M-H)$^-$. C$_{13}$H$_{15}$NO$_2$ requires 217.

(b) (E)-3-(5-(2,3-Dihydro)benzofuranyl)propenoic acid

Mass spectrum (API$^+$): Found 189 (M-H)$^-$. C$_{11}$H$_{10}$O$_3$ requires 190.

Description 10
1-(4-Bromophenyl)-2-pyrrolidinone

To a solution of 4-bromoaniline (10 g, 58 mmol) in dry THF (150 ml), under argon was added triethylamine (6 g, 59 mmol) and 4-chlorobutyrylchloride (8.2 g 58 mmol) at 5° C. The mixture was stirred at 5° C. for 40 mins and potassium tert-butoxide (16 g, 142 mmol) added in one portion. After 10 mins the mixture was warmed to 25° C. and stirred for 4 hours, then left to stand overnight. Water (10 ml) was added and the mixture stirred for 30 mins. The mixture was diluted with ethyl acetate (200 ml) and 3% $Na_2CO_3$ (aq) (120 ml). The aqueous layer was reextracted with ethyl acetate (100 ml) and the combined extracts dried over $Na_2SO_4$. The solvent was evaporated in vacuo to give a brown solid (12 g). Chromatography on silica gel (~200 g) using 30–60% ethyl acetate/hexane gradient elution gave the title compound as a yellow crystalline solid (10.24 g, 74%).

Mass spectrum ($API^+$): Found 240 ($MH^+$). $C_{10}H_{10}{}^{79}BrNO$ requires 239.

Description 11
(E)-3-(4-(1-(2-Oxo)pyrrolidinyl)phenyl)propenoic Acid

A mixture of 1-(4-bromophenyl)-2-pyrrolidinone (2.39 g, 10 mmol), acrylic acid (0.8 g, 11.1 mmol), palladium acetate (1.1 mg, 0.005 mmol), triphenylphosphine (26 mg, 0.1 mmol) and tri-n-butylamine (5 ml), was heated at 150° C. for 2.5 hrs. The mixture was allowed to cool to room temperature and then water (20 ml) was added, followed by careful addition of sodium hydrogen carbonate (2 g) with vigorous stirring. The mixture was then filtered and the filtrate washed with dichloromethane (10 ml). The aqueous layer was acidified to pH1 using 5N HCl, and the resultant precipitate filtered, washed with ether (10 ml), and dried to give the title compound as a yellow solid (1.24 g, 5.4 mmol), 54%).

Mass spectrum ($API^+$): Found 230 (M-H)⁻. $C_{13}H_{13}NO_3$ requires 231.

The following compounds were prepared in a similar manner to Description 11:

(a) (E)-3-(3-Acetamidophenyl)propenoic acid
$^1H$ NMR (DMSO) δ: 2.05 (3H, s), 6.40 (1H, d, J=15 Hz), 7.35 (2H, m), 7.55 (1H, d, J=15 Hz), 7.60 (1H, m), 7.85 (1H, br s), 10.10 (1H, s), 12.50 (1H, br s).

(b) (E)-3-(3-Dimethylaminophenyl)propenoic acid
$^1H$ NMR ($CDCl_3$) δ: 2.95 (6H, s), 6.45 (1H, d, J=15 Hz), 6.80 (1H, dd, J=8 Hz, 2 Hz), 6.85 (1H, br s), 6.95 (1H, d, J=8 Hz), 7.25 (2H, m), 7.75 (1H, d, J=15 Hz).

Description 12
2-(4-Phthalimidobutyl)-7-(2-thiophenesulfonyloxy)-1,2,3,4-tetrahydroisoquinoline A stirred mixture of 7-hydroxy-2-(4-phthalimidobutyl)-1,2,3,4-tetrahydroisoquinoline (2.94 g, 8.4 mmol) and triethylamine (1.4 ml, 10 mmol) in dichloromethane (75 ml) was treated with 2-thiophenesulfonyl chloride (1.69 g, 9.2 mmol). After stirring at room temperature for 18 h the mixture was washed with saturated aqueous sodium bicarbonate (100 ml). The aqueous layer was separated and extracted with dichloromethane (2×50 ml). The combined extracts were washed with brine, dried ($Na_2SO_4$) and evaporated in vacuo. The residue was chromatographed on silica using 30–100% ethyl acetate-pentane gradient elution to afford the title compound as a pale yellow oil (3.45 g, 83%).

$^1H$ NMR ($CDCl_3$) δ: 1.50–1.75 (4H, m), 2.52 (2H, t, J=7 Hz), 2.68 (2H, t, J=7 Hz), 2.84 (2H, t, J=7 Hz), 3.50 (2H, s), 3.74 (2H, t, J=7 Hz), 6.68 (1H, d, J=3 Hz), 6.75 (2H, dd, J=3, 8 Hz), 7.00 (1H, d, J=10 Hz), 7.08 (1H, m), 7.55 (1H, m), 7.70 (2H, m), 7.85 (2H, m).

The following compounds were prepared in a similar manner to Description 12:

(a) 7-Methylsulfonyloxy-2-(4-phthalimidobutyl)-1,2,3,4-tetrahydroisoquinoline
Mass spectrum ($API^+$): Found: 429 ($MH^+$). $C_{22}H_{24}N_2O_5S$ requires 428.

(b) 7-(4-Cyanophenylsulfonyloxy)-2-(4-phthalimidobutyl)-1,2,3,4-tetrahydroisoquinoline
$^1H$ NMR ($CDCl_3$) δ: 1.50–1.85 (4H, m), 2.55 (2H, t, J=5 Hz), 2.70 (2H, t, J=5 Hz), 2.85 (2H, t, J=5 Hz), 3.50 (2H, s), 3.75 (2H, t, J=5 Hz), 6.65 (2H, m), 7.00 (1H, d, J=10 Hz), 7.70 (2H, m), 7.75–7.90 (4H, m), 7.95 (2H, m).

Description 13
7-Methylsulfonamido-2-(4-phthalimidobutyl)-1,2,3,4-tetrahydroisoquinoline 7-Amino-2-(4-phthalimidobutyl)-1,2,3,4-tetrahydroisoquinoline (3 g, 8.6 mmol) was dissolved in dichloromethane (100 ml), and 2,6-lutidine (1.2 ml, 10.32 mmol) was added. To this methylsulfonyl chloride (0.73 ml, 9.46 mmol) was added dropwise. A further portion of 2,6-lutidine (0.6 ml, 5.16 mmol) and methylsulfonyl chloride (0.37 ml, 4.78 mmol) were later added. The mixture was partitioned between sodium bicarbonate solution (100 ml) and dichloromethane (3×50 ml). The combined extracts were dried ($Na_2SO_4$) and evaporated in vacuo. Chromatography of the residue on alumina with ethyl acetate +0–1% methanol gradient elution gave the title compound as an oil (1.8 g, 49%).

Mass spectrum ($API^+$): Found 428 ($MH^+$). $C_{22}H_{25}N_3O_4S$ requires 427.

The following compounds were prepared in a similar manner to Description 13:

(a) 7-(4-Cyanophenyl)sulfonamido-2-(4-phthalimidobutyl)-1,2,3,4-tetrahydroisoquinoline
Mass spectrum ($API^+$): Found 515 ($MH^+$). $C_{28}H_{26}N_4O_4S$ requires 514.

(b) 7-Phenylsulfonamido-2-(4-phthalimidobutyl)-1,2,3,4-tetrahydroisoquinoline
Mass spectrum ($API^+$): Found 490 ($MH^+$). $C_{27}H_{27}N_3O_4S$ requires 489.

Description 14
7-Bromo-1,2,3,4-tetrahydroisoquinoline

A mixture of 7-bromo-2-trifluoroacetyl-1,2,3,4-tetrahydroisoquinoline (G. E. Stokker, Tetrahedron Letters 1996, 37, 5453) (43.4 g, 0.14 mol), potassium carbonate (104.3 g, 0.75 mol), methanol (1 L) and water (150 ml) was heated at reflux for 1 h, then cooled and evaporated in vacuo. Residue was partitioned between water (1 L) and dichloromethane (4×200 ml). Combined extracts were dried ($Na_2SO_4$) and evaporated in vacuo to give an oil which was dissolved in hexane. The mixture was filtered and the filtrate evaporated in vacuo to give the title compound as an oil (17.7 g, 60%).

$^1H$ NMR ($CDCl_3$) δ: 1.77 (1H, br s), 2.73 (2H, t, J=7 Hz), 3.13 (2H, t, J=7 Hz), 3.98 (2H, s), 6.96 (1H, d, J=9 Hz), 7.16 (1H, d, J=2 Hz), 7.26 (1H, dd, J=9, 2 Hz).

The following compounds were prepared in a similar manner to Description 14:

(a) 7-Trifluoromethoxy-1,2,3,4-tetrahydroisoquinoline
Mass spectrum ($API^+$): Found 218 ($MH^+$). $C_{10}H_{10}F_3NO$ requires 217.

(b) 7-Cyano-1,2,3,4-tetrahydroisoquinoline
Mass spectrum ($API^+$): Found 159 ($MH^+$). $C_{10}H_{10}N_2$ requires 158.

Description 15
7-Nitro-1,2,3,4-tetrahydroisoquinoline

Prepared from 7-Nitro-2-trifluoroacetyl-1,2,3,4-tetrahydroisoquinoline (G. E. Stokker, Tetrahedron Letters 1996, 37, 5453) using a procedure similar to Description 14 in 80% yield.

$^1$H NMR (CDCl$_3$) δ: 1.72 (1H, s), 2.89 (2H, t, J=6 Hz), 3.18 (2H, t, J=6 Hz), 4.09 (2H, s), 7.24 (1H, d, J=10 Hz), 7.89–8.06 (2H, m).

Description 16
7-Amino-2-(4-phthalimidobutyl)-1,2,3,4-tetrahydroisoquinoline A mixture of 5% palladium on carbon paste (3.44 g), 7-nitro-2-(4-phthalimidobutyl)-1,2,3,4-tetrahydroisoquinoline (19.15 g, 0.05 mol), ethanol (791 ml) and water (69 ml) was hydrogenated at 50 psi and 30° C. for 6 days. The reaction mixture was then filtered through Kieselguhr and evaporated in vacuo to give the title compound as an oil (18.04 g, 100%).

Mass spectrum (API$^+$): Found 350 (MH$^+$). $C_{21}H_{23}N_3O_2$ requires 349.

Description 17
(4-Trifluoroacetamido)butyraldehyde

To a solution of 4-aminobutyraldehyde diethyl acetal (16.10 g, 0.10 mmol) and triethylamine (18.06 ml, 0.12 mol) in dichloromethane (150 ml) at 0° C. was added a solution of trifluoroacetic anhydride (16.9 ml, 0.11 mol) in dichloromethane (60 ml). The reaction mixture was warmed to room temperature and stirred for 3 h, then partitioned between 5% aq NaHCO$_3$ (400 ml) and dichloromethane (400 ml). The aqueous layer was extracted further with dichloromethane (3×100 ml), the combined extracts were dried (Na$_2$SO$_4$) and evaporated in vacuo to afford a pale yellow oil which was added to a stirred mixture of THF (300 ml) and water (500 ml). 5N Sulfuric acid (2.27 ml) was added and the reaction mixture left to stir at room temperature for 18 h. Saturated aqueous sodium bicarbonate (500 ml) was added and the product was extracted into dichloromethane (4×100 ml). The combined organic extracts were dried (Na$_2$SO$_4$) and evaporated in vacuo to afford the title compound as a yellow oil (15.42 g, 65%).

$^1$H NMR (CDCl$_3$) δ: 1.95 (2H, m), 2.62 (2H, t, J=8 Hz), 3.38 (2H, m), 7.54–7.80 (1H, br s), 9.77 (1H, s).

Description 18
7-Acetyl-2-(4-trifluoroacetamidobutyl)-1,2,3,4-tetrahydroisoquinoline The title compound was prepared in 37% yield by treating 7-acetyl-1,2,3,4-tetrahydroisoquinoline with (4-trifluoroacetamido)butyraldehyde using a procedure similar to that of Description 3.

Mass spectrum (API$^+$): Found 343 (MH$^+$). $C_{17}H_{21}F_3N_2O_2$ requires 342.

The following compounds were prepared in a similar manner to Description 18:

(a) 7-Cyano-2-(4-trifluoroacetamidobutyl)-1,2,3,4-tetrahydroisoquinoline

Mass spectrum (API$^+$): Found 326 (MH$^+$). $C_{16}H_{18}F_3N_3O$ requires 325.

(b) 2-(4-Trifluoroacetamidobutyl)-1,2,3,4-tetrahydroisoquinoline

Mass spectrum (API$^+$): Found 301 (MH$^+$). $C_{15}H_{19}F_3N_2O$ requires 300.

(c) 7-Methylaminosulfonyl-2-(4-trifluoroacetamidobutyl)-1,2,3,4-tetrahydroisoquinoline Mass spectrum (API$^+$): Found 394 (MH$^+$). $C_{16}H_{22}F_3N_3O_3S$ requires 393.

Description 19
7-Acetyl-2-(4-aminobutyl)-1,2,3,4-tetrahydroisoquinoline

A solution of 7-acetyl-2-(4-trifluoroacetamidobutyl)-1,2,3,4-tetrahydroisoquinoline (0.360 g, 1.05 mmol) was added to a stirred mixture of methanol (10 ml), water (1.5 ml) and potassium carbonate (0.769 g, 5.56 mmol) and heated at reflux for 1 h. The mixture was cooled then evaporated in vacuo and the residue partitioned between water (100 ml) and dichloromethane (50 ml). The aqueous phase was washed with dichloromethane (2×50 ml). The combined organic extracts were dried (Na$_2$SO$_4$) and evaporated in vacuo to afford the title compound as a yellow oil (0.178 g, 68%).

$^1$H NMR (CDCl$_3$) δ: 1.44–1.70 (4H, m), 1.75–1.92 (2H, br s), 2.56 (5H, m), 2.73 (4H, m), 2.95 (2H, t, J=4 Hz), 3.67 (2H, s), 7.18 (1H, d, J=6 Hz), 7.63 (1H, s), 7.71 (1H, d, J=6 Hz).

The following compounds were prepared in a similar manner to Description 19:

(a) 2-(4-Aminobutyl)-7-cyano-1,2,3,4-tetrahydroisoquinoline

Mass spectrum (API$^+$): Found 230 (MH$^+$). $C_{14}H_{19}N_3$ requires 229.

(b) 2-(4-Aminobutyl)-1,2,3,4-tetrahydroisoquinoline

Mass spectrum (API$^+$): Found 205 (MH$^+$). $C_{13}H_{20}N_2$ requires 204.

(c) 2-(4-Aminobutyl)-7-methylaminosulfonyl-1,2,3,4-tetrahydroisoquinoline

Mass spectrum (API$^+$): Found 298 (MH$^+$). $C_{14}H_{23}N_3O_2S$ requires 297.

Description 20
7-Bromo-2-methoxycarbonyl-1,2,3,4-tetrahydroisoquinoline

To a mixture of 7-bromo-1,2,3,4-tetrahydroisoquinoline (19.33 g, 0.091 mol) and triethylamine (16.6 ml, 0.119 mol) in dichloromethane (300 ml) was added a solution of methyl chloroformate (8.5 ml; 0.109 mol) in dichloromethane (30 ml), dropwise with ice cooling. Mixture was stirred for 3 h at room temperature then partitioned between saturated aqueous NaHCO$_3$ (100 ml) and dichloromethane (100 ml). Organic phase was dried (Na$_2$SO$_4$) and evaporated in vacuo to give an oil. Chromatography on silica with 30% ethyl acetate-hexane as eluant gave the title compound as an oil (15.25 g, 62%).

$^1$H NMR (CDCl$_3$) δ: 2.80 (2H, m), 3.69 (2H, m), 3.76 (3H, s), 4.59 (2H, s), 7.00 (1H, d, J=9 Hz), 7.28 (2H, m).

Description 21
7-Cyano-2-methoxycarbonyl-1,2,3,4-tetrahydroisoquinoline

A mixture of 7-bromo-2-methoxycarbonyl-1,2,3,4-tetrahydroisoquinoline (12.0 g, 0.044 mol), copper (I) cyanide (8.7 g, 0.097 mol) and N-methyl-2-pyrrolidinone (100 ml) was heated at reflux for 4 h, cooled, then partitioned between dilute aqueous ammonia (500 ml) and ethyl acetate (300 ml). Organic phase was washed with dilute aqueous ammonia (100 ml), water (4×100 ml), then dried (Na$_2$SO$_4$) and evaporated in vacuo to give the title compound as an oil (7.89 g, 83%).

Mass spectrum (API$^+$): Found 217 (MH$^+$). $C_{12}H_{12}N_2O_2$ requires 216.

The following compound was prepared in a similar manner to Description 21:

(a) 7-Cyano-2-trifluoroacetyl-1,2,3,4-tetrahydroisoquinoline

Mass spectrum (API$^+$): Found 253 (M-H)$^-$. $C_{12}H_9F_3N_2O$ requires 254.

Description 22

7-Hydroxymethyl-2-methoxycarbonyl-1,2,3,4-tetrahydroisoquinoline

A mixture of 7-cyano-2-methoxycarbonyl-1,2,3,4-tetrahydroisoquinoline (6.06 g, 28 mmol), Raney nickel (50%, 12.2 g) and aqueous formic acid (75%; 80 ml) was heated at reflux for 1 h. Mixture was filtered through kieselguhr and the filtrate partitioned between water (300 ml) and dichloromethane (4×100 ml). Combined organic extracts were washed with saturated aqueous NaHCO$_3$ (200 ml), dried (Na$_2$SO$_4$) and evaporated in vacuo to give an oil (4.85 g). The latter was dissolved in methanol (100 ml) and treated with sodium borohydride (0.84 g, 22.1 mmol). Mixture was stirred at room temperature for 3 h then treated with 5N HCl (5 ml). Resulting mixture was partitioned between saturated aqueous NaHCO$_3$ (200 ml) and dichloromethane (4×50 ml). Combined extracts were dried (Na$_2$SO$_4$) and evaporated in vacuo to give the title compound as an oil (4.65 g, 75%).

$^1$H NMR (CDCl$_3$) δ: 1.96 (1H, br t, J=6 Hz), 2.83 (2H, t, J=7 Hz), 3.69 (2H, m), 3.75 (3H, s), 4.60 (2H, s), 4.65 (2H, d, J=6 Hz), 7.12 (3H, m).

Description 23

2-Methoxycarbonyl-7-phenylsulfonylmethyl-1,2,3,4-tetrahydroisoquinoline

To a stirred solution of 7-hydroxymethyl-2-methoxycarbonyl-1,2,3,4-tetrahydroisoquinoline (4.65 g, 20.9 mmol) and triethylamine (3.26 ml, 22.1 mmol) in dichloromethane (200 ml) at 0° C. was added a solution of methanesulfonyl chloride (1.67 ml; 22.1 mmol) in dichloromethane (20 ml). Mixture was stirred at room temperature for 18 h then partitioned between saturated aqueous NaHCO$_3$ (200 ml) and dichloromethane (3×50 ml). Combined extracts were dried (Na$_2$SO$_4$) and evaporated in vacuo to give an oil (6.1 g). The latter was dissolved in acetone (200 ml) and treated with sodium iodide (3.35 g, 22.4 mmol). Resulting mixture was stirred at room temperature for 3 h, then ether (300 ml) was added and the resulting solid filtered off. The filtrate was evaporated in vacuo to give a solid (6.1 g). An aliquot of the latter (3.0 g) was dissolved in dimethylformamide (60 ml) and treated with sodium phenylsulfinate (1.65 g, 10 mmol). Resulting solution was stirred at room temperature for 18 h then partitioned between ethyl acetate (300 ml) and water (5×100 ml). Organic phase was dried (Na$_2$SO$_4$) and evaporated in vacuo to give an oil. Chromatography on silica with 10–100% ethyl acetate-hexane gradient elution gave the title compound as a colourless solid (2.3 g, 65%).

Mass spectrum (API$^+$): Found 346 (MH$^+$). $C_{18}H_{19}NO_4S$ requires 345.

Description 24

7-Phenylsulfonylmethyl-1,2,3,4-tetrahydroisoquinoline

A mixture of 2-methoxycarbonyl-7-phenylsulfonylmethyl-1,2,3,4-tetrahydroisoquinoline (21.5 g, 6.2 mmol), sodium hydroxide (20 g, 0.5 mol) and methanol (250 ml) was heated at reflux for 64 h. The mixture was cooled and evaporation in vacuo, then the residue was partitioned between water (100 ml) and dichloromethane (5×50 ml). Combined organic extracts were dried (Na$_2$SO$_4$) and evaporated in vacuo to give the title compound as a colourless solid (1.77 g, 99%).

Mass spectrum (API$^+$): Found 288 (MH$^+$). $C_{16}H_{17}NO_2S$ requires 287.

The following compound was prepared in a similar manner to Description 24:

(a) 7-Methylsulfonylmethyl-1,2,3,4-tetrahydroisoquinoline

Mass spectrum (API$^+$): Found 226 (MH$^+$). $C_{11}H_{15}NO_2S$ requires 225.

Description 25

2-Methoxycarbonyl-7-methylthiomethyl-1,2,3,4-tetrahydroisoquinoline

To a stirred solution of 7-hydroxymethyl-2-methoxycarbonyl-1,2,3,4-tetrahydroisoquinoline (4.65 g, 20.9 mmol) and triethylamine (3.26 ml, 22.1 mmol) in dichloromethane (200 ml) at 0° C. was added a solution of methanesulfonyl chloride (1.67 ml; 22.1 mmol) in dichloromethane (20 ml). Mixture was stirred at room temperature for 18 h then partitioned between saturated aqueous NaHCO$_3$ (200 ml) and dichloromethane (3×50 ml). Combined extracts were dried (Na$_2$SO$_4$) and evaporated in vacuo to give an oil (6.1 g). The latter was dissolved in acetone (200 ml) and treated with sodium iodide (3.35 g, 22.4 mmol). Resulting mixture was stirred at room temperature for 3 h, then ether (300 ml) was added and the resulting solid filtered off. The filtrate was evaporated in vacuo to give a solid (6.1 g). An aliquot of the latter (2.64 g, 7.98 mmol) was dissolved in dimethylformamide (20 ml) and treated with sodium methylthiolate (0.59 g, 8.38 mmol), then stirred at room temperature for 4 h. The mixture was evaporated in vacuo and the residue partitioned between water (100 ml) and dichloromethane (4×30 ml). The combined organic extracts were dried (Na$_2$SO$_4$), then evaporated in vacuo to give an oil. Chromatography on silica with 10–50% ethyl acetate-hexane gradient elution gave the title compound (1.01 g, 44%).

$^1$H NMR (CDCl$_3$) δ: 2.02 (3H, s), 2.73 (2H, t, J=7 Hz), 3.63 (2H, s), 3.69 (2H, m), 3.74 (3H, s), 4.62 (2H, br s), 7.00–7.13 (3H, m).

Description 26

2-Methoxycarbonyl-7-methylsulfonylmethyl-1,2,3,4-tetrahydroisoquinoline

To a stirred solution of 2-methoxycarbonyl-7-methylthiomethyl-1,2,3,4-tetrahydroisoquinoline (0.90 g, 3.59 mmol) in acetic acid (10 ml) was added a solution of peracetic acid in acetic acid (36% w/w; 1.4 ml; 7.6 mmol) with ice cooling. Reaction mixture was stirred at room temperature for 18 h, then partitioned between saturated aqueous NaHCO$_3$ (200 ml) and dichloromethane (3×50 ml). Combined organic extracts were dried (Na$_2$SO$_4$) and evaporated in vacuo to give an oil (1.1 g). Chromatography on silica with 20–100% ethyl acetate-hexane gradient elution gave the title compound (0.23 g, 23%).

Mass spectrum (API$^+$): Found 284 (MH$^+$). $C_{13}H_{17}NO_4S$ requires 283.

Description 27

2-Trifluoroacetyl-7-trifluoromethoxy-1,2,3,4-tetrahydroisoquinoline

Prepared in two steps from 4-trifluoromethoxyphenethylamine using a method similar to that described in G. E. Stokker, Tetrahedron Letters 1996, 37, 5453, in 69% yield.

Mass spectrum (API$^+$): Found 314 (MH$^+$). $C_{12}H_9F_6NO_2$ requires 313.

Description 28
7-Methylaminosulfonyl-1,2,3,4-tetrahydroisoquinoline, Hydrochloride To a solution of 2-acetyl-1,2,3,4-tetrahydroisoquinoline (73 g) in dry dichloromethane (500 ml) under argon at −75° C., was added chlorosulfonic acid (120 ml) dropwise. The resulting brown solution was allowed to stir from −75° C. to room temperature over 20 h. It was then poured into 2 L of crushed ice and extracted with dichloromethane (2×500 ml). The combined organic layers were washed with brine (2×500 ml), dried ($Na_2SO_4$) and evaporated to dryness in vacuo to give an amber oil (115 g). To a solution of the latter (51 g) in dry THF (200 ml) at 0° C., was added a 2M methylamine solution in THF (200 ml). The resulting solution was allowed to stir at room temperature for 18 h. Solvent was evaporated in vacuo to give an oil which was dissolved in dichloromethane (800 ml) and washed with brine (500 ml), dried ($Na_2SO_4$) and evaporated to give an amber oil. The latter was treated with hot ethyl acetate (300 ml) to give a colourless solid precipitate which was filtered and dried in vacuo (12 g). The solid (6 g) was stirred at reflux in 3.7M hydrochloric acid (190 ml) for 18 h. The solution was cooled to room temperature and neutralised with aqueous potassium carbonate. The water was removed on a freeze-dryer and the resulting solid was repeatedly washed with dichloromethane (4×500 ml). The combined organic washings were evaporated in vacuo to afford a colourless solid (4.8 g) which was treated with ethereal HCl in methanol. Recrystallisation from ethanol gave the title compound (3.5 g).

Mass spectrum ($API^+$): Found 227 ($MH^+$). $C_{10}H_{14}N_2O_2S$ requires 226. $^1H$ NMR (MeOH-$d_4$) δ: 2.33 (3H, s), 2.82 (2H, m), 3.07 (2H, m), 3.97 (2H, br s), 7.19 (1H, d, J=8 Hz), 7.40–7.50 (2H, m)

EXAMPLE 1

(E)-7-Methoxy-2-(4-(3-phenylpropenoyl)aminobutyl)-1,2,3,4-tetrahydroisoquinoline 1-Ethyl-3-(3-dimethylaminopropyl)carbodiimide hydrochloride (0.41 g, 2.14 mmol) was added to a solution of trans-cinnamic acid (0.317 g, 2.14 mmol), 2-(4-aminobutyl)-7-methoxy-1,2,3,4-tetrahydroisoquinoline (0.5 g, 2.14 mmol) and 1-hydroxybenzotriazole (0.1 g, 0.7 mmol) in dichloromethane (8 ml). The mixture was shaken for 18 h, saturated aqueous potassium carbonate (5 ml) added and shaking continued for a further 1 h. The organic layer was chromatographed on silica gel using 10–100% ethyl acetate-hexane gradient elution to afford the title compound as a yellow gum (0.53 g, 68%).

Mass spectrum ($API^+$): 365 ($MH^+$). $C_{23}H_{28}N_2O_2$ requires 364. $^1H$ NMR (CDCl$_3$) δ: 1.70 (4H, m), 2.55 (2H, t, J=7 Hz), 2.75 (2H, t, J=7 Hz), 2.90 (2H, t, J=7 Hz), 3.40 (2H, m), 3.65 (2H, s), 3.75 (3H, s,), 6.0 (1H, d, J=15 Hz), 6.60 (1H, d, J=2 Hz), 6.75 (1H, dd, J=2 Hz, 8 Hz), 7.05 (1H, d, J=8 Hz), 7.15 (2H, m), 7.25 (3H, m), 7.50 (1H, d, J=15 Hz), 7.95 (1H, br m).

EXAMPLE 2

(E)-7-Hydroxy-2-(4-(3-phenylpropenoyl)aminobutyl)-1,2,3,4-tetrahydroisoquinoline (E)-7-Methoxy-2-(4-(3-phenylpropenoyl)aminobutyl)-1,2,3,4-tetrahydroisoquinoline (0.46 g, 1.25 mmol) in dichloromethane (3 ml) was treated with 1N hydrogen chloride in diethyl ether (3 ml) and the mixture evaporated in vacuo to afford the hydrochloride salt. The hydrochloride salt (0.5 g, 1.25 mmol) in dichloromethane (40 ml) was ice cooled as a solution of boron tribromide in dichloromethane (10 ml, 1M solution, 10 mmol) was added dropwise. After stirring at room temperature for 18 h. the mixture was added to ice and 0.880 ammonia (100 ml) and the mixture stirred for 1 h then extracted into dichloromethane (2×100 ml). Combined organics were washed with brine (50 ml), dried ($Na_2SO_4$) and evaporated in vacuo to afford the beige solid (0.43 g).

Mass spectrum ($API^+$): 351 ($MH^+$). $C_{22}H_{26}N_2O_2$ requires 350. $^1H$ NMR (CDCl$_3$) δ: 1.70 (4H, m), 2.50 (2H, m), 2.75 (2H, m), 2.80 (2H, m), 3.40 (2H, m), 3.45 (2H, s), 6.15 (1H, d, J=15 Hz), 6.45 (1H, br d), 6.70 (1H, dd, J=2 Hz, 8 Hz), 6.90 (1H, d, J=8 Hz), 7.25 (6H, m), 7.55 (1H, d, J=15 Hz), 7.70 (1H, br m).

EXAMPLE 3

(E)-2-(4-(3-Phenylpropenoyl)aminobutyl)-7-trifluoromethylsulfonyloxy-1,2,3,4-tetrahydroisoquinoline Trifluoromethanesulfonic anhydride (0.26 ml, 1.52 mmol) was added dropwise with stirring to an ice cooled solution of (E)-7-hydroxy-2-(4-(3-phenylpropenoyl)aminobutyl)-1,2,3,4-tetrahydroisoquinoline (0.41 g, 1.17 mmol) in anhydrous pyridine (5 ml). After stirring at room temperature for 18 h the reaction mixture was poured into 10% aqueous copper (II) sulfate (100 ml). The mixture was extracted with ethyl acetate (2×75 ml). Combined extracts were washed with 10% aqueous copper (II) sulfate (2×50 ml), water (50 ml), dried ($Na_2SO_4$) and evaporated in vacuo. The residue was chromatographed on silica using 10–100% ethyl acetate-hexane gradient elution to afford the title compound (0.205 g, 43%).

Mass spectrum ($API^+$): 483 ($MH^+$). $C_{23}H_{25}F_3N_2O_4S$ requires 482. $^1H$ NMR (CDCl$_3$) δ: 1.70 (4H, m), 2.60 (2H, t, J=7 Hz), 2.75 (2H, t, J=7 Hz), 2.95 (2H, t, J=7 Hz), 3.40 (2H, m), 3.65 (2H, s), 6.20 (1H, d, J=15 Hz), 6.70 (1H, br m), 6.95 (1H, d, J=2 Hz), 7.15 (1H, dd, J=2 Hz, 8 Hz), 7.15 (1H, d, J=8 Hz), 7.3 (5H, s), 7.60 (1H, d, J=15 Hz).

EXAMPLE 4

(E)-2-(4-(3-(3-Nitrophenyl)propenoyl)aminobutyl)-7-trifluoromethylsulfonyloxy-1,2,3,4-tetrahydroisoquinoline Prepared from 2-(4-aminobutyl)-7-trifluoromethylsulfonyloxy-1,2,3,4-tetrahydroisoquinoline (0.4 g, 1.14 mmol) and trans-3-nitrocinnamic acid (0.22 g, 1.14 mmol) using a procedure similar to that of Example 1 (0.362 g, 60%).

Mass spectrum ($API^+$): 528 ($MH^+$). $C_{23}H_{24}F_3N_3O_6S$ requires 527. $^1H$ NMR (CDCl$_3$) δ: 1.75 (4H, br s), 2.60 (2H, t, J=7 Hz), 2.80 (2H, t, J=7 Hz), 3.00 (2H, t, J=7 Hz), 3.45 (2H, m), 3.70 (2H, s), 6.30 (1H, d, J=15 Hz), 6.85 (1H, m), 6.95 (1H, s), 7.05 (1H, dd, J=8 Hz, 2 Hz), 7.20 (1H, d, J=8 Hz), 7.50–7.70 (2H, m), 7.65 (1H, d, J=15 Hz), 8.20 (1H, dd, J=8 Hz, 2 Hz), 8.35 (1H, br s).

The following compounds were prepared in a similar manner to Example 4:

(a) (E)-2-(4-(3-(4-Methoxyphenyl)propenoyl)aminobutyl)-7-trifluoromethylsulfonyloxy-1,2,3,4-tetrahydroisoquinoline Mass spectrum ($API^+$): 513 ($MH^+$). $C_{24}H_{27}F_3N_2O_5S$ requires 512. $^1H$ NMR (CDCl$_3$) δ: 1.70 (4H, m), 2.60 (2H, t, J=7 Hz), 2.75 (2H, t, J=7 Hz), 2.95 (2H, t, J=7 Hz), 3.40 (2H, m), 3.65 (2H, s), 3.85 (3H, s), 6.10 (1H, d, J=15 Hz), 6.60 (1H, br t, J=6 Hz), 6.85 (2H, d, J=8 Hz), 6.95 (1H, d, J=2 Hz), 7.05 (1H, dd, J=8 Hz, 2 Hz), 7.20 (1H, d, J=8 Hz), 7.30 (2H, d, J=8 Hz), 7.55 (H, d, J=15 Hz).

(b) (E)-2-(4-(3-(4-Bromophenyl)propenoyl)aminobutyl)-7-trifluoromethylsulfonyloxy-1,2,3,4-tetrahydroisoquinoline Mass spectrum ($API^+$): 561, 563 ($MH^+$). $C_{23}H_{24}BrF_3N_2O_4S$ requires 560, 562. $^1H$ NMR (CDCl$_3$) δ:

1.70 (4H, m), 2.60 (2H, t, J=7 Hz), 2.75 (2H, t, J=7 Hz), 2.95 (2H, t, J=7 Hz), 3.40 (2H, m), 3.70 (2H, s), 6.15 (1H, d, J=15 Hz), 6.75 (1H, br m), 6.95 (1H, d, J=2 Hz), 7.05 (1H, dd, J=8 Hz, 2 Hz), 7.20 (3H, m), 7.45–7.55 (3H, m).

(c) (E)-2-(4-(3-(2-Thienyl)propenoyl)aminobutyl)-7-trifluoromethylsulfonyloxy-1,2,3,4-tetrahydroisoquinoline Mass spectrum: (API$^+$): 489 (MH$^+$). $C_{21}H_{23}F_3N_2O_4S_2$ requires 488. $^1$H NMR (CDCl$_3$) δ: 1.70 (4H, m), 2.55 (2H, t, J=7 Hz), 2.75 (2H t, J=7 Hz), 2.95 (2H, t, J=7 Hz), 3.40 (2H, m), 3.65 (2H, s), 6.05 (1H, d, J=15 Hz), 6.60 (1H, br m), 7.05 (3H, m), 7.20 (2H, m), 7.30 (1H, m), 7.70 (1H, d, J=15 Hz)

(d) (E)-2-(4-(3-(2-Naphthyl)propenyl)aminobutyl)-7-trifluoromethylsulfonyloxy-1,2,3,4-tetrahydroisoquinoline Mass spectrum (API$^+$): 533 (MH$^+$). $C_{27}H_{27}F_3N_2O_4S$ requires 532. $^1$H NMR (CDCl$_3$) δ: 1.72 (4H, m), 2.59 (2H, m), 2.76 (2H, t, J=6 Hz), 2.95 (2H, m), 3.44 (2H, m), 3.66 (2H, s), 6.31 (1H, d, J=15 Hz), 6.66 (1H, m), 7.01 (2H, m), 1.17 (1H, d, J=8 Hz), 7.46 (3H, m), 7.78 (5H, m).

(e) (E)-2-(4-(3-(3-Furyl)propenoyl)aminobutyl)-7-trifluoromethylsulfonyloxy-1,2,3,4-tetrahydroisoquinoline Mass spectrum (API$^+$): 473 (MH$^+$). $C_{21}H_{23}F_3N_2O_5S$ requires 472. $^1$H NMR (CDCl$_3$) δ: 1.70 (4H, m), 2.57 (2H, m), 2.64 (2H, t, J=7 Hz), 2.94 (2H, m), 3.41 (2H, m), 3.66 (2H, s), 5.94 (1H, d, J=15 Hz), 6.33 (1H, m), 6.50 (1H, m), 6.97 (1H, m), 7.05 (1H, dd, J=9 Hz, 3 Hz), 7.18 (1H, d, J=8 Hz), 7.38 (1H, s), 7.48 (1H, d, J=15 Hz), 7.56 (1H, s).

(f) (E)-2-(4-(3-(4-Chlorophenyl)propenoyl)aminobutyl)-7-trifluoromethylsulfonyloxy-1,2,3,4-tetrahydroisoquinoline Mass spectrum (API$^+$): 517 (MH$^+$). $C_{23}H_{24}^{35}ClF_3N_2O_4S$ requires 516. $^1$H NMR (CDCl$_3$) δ: 1.69 (4H, m), 2.56 (2H, m), 2.76 (2H, m), 2.92 (2H, m), 3.43 (2H, m), 3.66 (2H, s), 6.13 (1H, d, J=15 Hz), 6.70 (1H, m), 7.02 (2H, m), 7.21 (5H, m), 7.52 (1H, d, J=15 Hz).

(g) (E)-2-(4-(3-(4-Dimethylaminophenyl)propenoyl) aminobutyl)-7-trifluoromethylsulfonyloxy-1,2,3,4-tetrahydroisoquinoline Mass spectrum (API$^+$): 526 (MH$^+$). $C_{25}H_{30}F_3O_4S$ requires 525. $^1$H NMR (CDCl$_3$) δ: 1.69 (4H, m), 2.57 (2H, m), 2.76 (2H, t, J=7 Hz), 2.94 (2H, m), 3.01 (6H, s), 3.42 (2H, m), 3.66 (2H, s), 5.98 (1H, d, J=16 Hz), 6.44 (1 h, m), 6.64 (2H, d, J=8 Hz), 6.98 (1H, m), 7.06 (1H, dd, J=8 Hz, 2 Hz), 7.21 (3H, m), 7.52 (1H, d, J=16 Hz).

(h) (E)-2-(4-(3-(3,4-Methylenedioxyphenyl)propenoyl) aminobutyl)-7-trifluoromethylsulfonyloxy-1,2,3,4-tetrahydroisoquinoline Mass spectrum (API$^+$): 527 (MH$^+$). $C_{24}H_{25}F_3N_2O_6S$ requires 526. $^1$H NMR (CDCl$_3$) δ: 1.70 (4H, m), 2.18 (2H, s), 2.56 (2H, m), 2.76 (2H, m), 2.95 (2H, m), 3.42 (2H, m), 3.66 (2H, s), 5.99 (1H, d, J=16 Hz), 6.67 (1H, m), 6.76 (2H, d, J=8 Hz), 6.86 (1H, m), 6.96 (1H, m), 7.06 (1H, dd, J=8 Hz, 2 Hz), 7.19 (1H, d, J=8 Hz), 7.47 (1H, d, J=16 Hz).

(i) (E)-2-(4-(3-(3-(1-Methyl)indolyl)propenoyl) aminobutyl)-7-trifluoromethylsulfonyloxy-1,2,3,4-tetrahydroisoquinoline Mass spectrum (API$^+$): Found 536 (MH$^+$). $C_{26}H_{28}F_3N_3O_4S$ requires 535. $^1$H NMR (CDCl$_3$) δ: 1.6 (4H, m), 2.6 (2H, m), 2.75 (2H, t, J=7 Hz), 2.95 (2H, m), 3.45 (2H, m ), 3.67 (2H, s), 3.81 (3H, s), 6.0 (1H, m), 6.28 (1H, d, J=15 Hz), 6.94 (1H, d, J=2 Hz), 7.02 (1H, dd, J=9 Hz, 2 Hz), 7.1–7.4 (5H, m), 7.8 (2H, m).

(j) (E)-2-(4-(3-(1-Naphthyl)propenoyl)aminobutyl)-7-trifluoromethylsulfonyloxy-1,2,3,4-tetrahydroisoquinoline Mass spectrum (API$^+$): Found 533 (MH$^+$). $C_{27}H_{27}F_3N_2O_4S$ requires 532. $^1$H NMR (CDCl$_3$) δ: 1.74 (4H, m), 2.58 (2H, m), 2.76 (2H, m), 2.92 (2H, m), 3.47 (2H, m), 3.67 (2H, s), 6.23 (1H, d, J=15 Hz), 6.80 (1H, m), 6.95 (2H, m), 7.10 (1H, d, J=8 Hz), 7.44 (2H, m), 7.54 (2H, m), 7.86 (2H, m), 8.21 (1H, m), 8.41 (1H, d, J=15 Hz).

(k) (E)-2-(4-(3-(2-Methylphenyl)propenoyl)aminobutyl)-7-trifluoromethylsulfonyloxy-1,2,3,4-tetrahydroisoquinoline Mass spectrum (API$^+$): Found 497 (MH$^+$). $C_{24}H_{27}F_3N_2O_4S$ requires 496. $^1$H NMR (CDCl$_3$) δ: 1.71 (4H, m), 2.40 (3H, s), 2.58 (2H, m), 2.76 (2H, m), 2.95 (2H, m), 3.43 (2H, m), 3.66 (2H, s), 6.08 (1H, d, J=15 Hz), 6.62 (1H, m), 6.95 (1H, m), 7.02 (1H, m), 7.22 (5H, m), 7.87 (1H, d, J=15 Hz).

(l) (E)-2-(4-(3-(3-Cyanophenyl)propenoyl)aminobutyl)-7-trifluoromethylsulfonyloxy-1,2,3,4-tetrahydroisoquinoline Mass spectrum (API$^+$): Found 508 (MH$^+$). $C_{24}H_{24}F_3N_3O_4S$ requires 507. $^1$H NMR (CDCl$_3$) δ: 1.72 (4H, m), 2.59 (2H, m), 2.78 (2H, m), 2.96 (2H, m), 3.43 (2H, m), 3.67 (2H, s), 6.18 (1H, d, J=15 Hz), 6.84 (1H, m), 6.96 (1H, d, J=2 Hz), 7.07 (1H, dd, J=7, 2 Hz), 7.22 (1H, d, J=7 Hz), 7.49 (3H, m), 7.62 (2H, m).

(m) (E)-2-(4-(3-(2-Quinolinyl)propenoyl)aminobutyl)-7-trifluoromethylsulfonyloxy-1,2,3,4-tetrahydroisoquinoline Mass spectrum (API$^+$): Found 534 (MH$^+$). $C_{26}H_{26}F_3N_3O_4S$ requires 533. $^1$H NMR (CDCl$_3$) δ: 1.71 (4H, m), 2.58 (2H, m), 2.77 (2H, m), 2.96 (2H, m), 3.47 (2H, m), 3.66 (2H, s), 6.58 (1H, m), 6.95 (3H, m), 7.15 (1H, d, J=7 Hz), 7.44 (1H, d, J=8 Hz), 7.55 (1H, m), 7.77 (3H, m), 8.06 (1H, d, J=8 Hz), 8.16 (1H, d, J=8 Hz).

(n) (E)-2-(4-(3-(2-Methoxyphenyl)propenoyl) aminobutyl)-7-trifluoromethylsulfonyloxy-1,2,3,4-tetrahydroisoquinoline Mass spectrum (API$^+$): Found 513 (MH$^+$). $C_{24}H_{27}F_3N_2O_5S$ requires 512. $^1$H NMR (CDCl$_3$) δ: 1.68 (4H, m), 2.56 (2H, m), 2.75 (2H, m), 2.93 (2H, m), 3.43 (2H, m), 3.65 (2H, s), 3.86 (3H, s), 6.34 (1H, d, J=15 Hz), 6.90 (4H, m), 7.02 (1 h, dd, J=8, 2 Hz), 7.16 (1H, d, J=8 Hz), 7.31 (2H, m), 7.83 (1H, d, J=15 Hz).

(o) (E)-2-(4-(3-(3-Indolyl)propenoyl)aminobutyl)-7-trifluoromethylsulfonyloxy-1,2,3,4-tetrahydroisoquinoline Mass spectrum (API$^+$): Found 522 (MH$^+$). $C_{25}H_{26}F_3N_3O_4S$ requires 521. $^1$H NMR (CDCl$_3$) δ: 1.65 (4H, m), 2.51 (2H, m), 2.69 (2H, t, J=7 Hz), 2.89 (2H, t, J=7 Hz), 3.45 (2H, m), 3.58 (2H, s), 6.35 (1H, d, J=16 Hz), 6.36 (1H, m), 6.90 (1H, d, J=2 Hz), 7.00 (1H, dd, J=9, 2 Hz), 7.05–7.46 (5H, m), 7.85 (2H, m), 9.20 (1H, br s).

(p) (E)-2-(4-(3-(2-Benzofuranyl)propenoyl)aminobutyl)-7-trifluoromethylsulfonyloxy-1,2,3,4-tetrahydroisoquinoline Mass spectrum (API$^+$): Found 523 (MH$^+$). $C_{25}H_{25}F_3N_2O_5S$ requires 522. $^1$H NMR (CDCl$_3$) δ: 1.68 (4H, m), 2.54 (2H, m), 2.73 (2H, t, J=7 Hz), 2.92 (2H, t, J=7 Hz), 3.43 (2H, m), 3.62 (2H, s), 6.45 (1H, d, J=16 Hz), 6.61 (1H, br s), 6.82 (1H, s),6.95 (1H, d, J=2 Hz), 7.01 (1H, dd, J=9, 2 Hz), 7.08–7.59 (6H, m).

(q) (E)-2-(4-(3-(4-Acetylphenyl)propenoyl)aminobutyl)-7-trifluoromethylsulfonyloxy-1,2,3,4-tetrahydroisoquinoline Mass spectrum (API$^+$): Found 525 (MH$^+$). $C_{25}H_{27}F_3N_2O_5S$ requires 524 $^1$H NMR (CDCl$_3$) δ: 1.70 (4H, m), 2.60 (2H, m), 2.65 (3H, s), 2.75 (2H, t, J=6 Hz), 2.95 (2H, t, J=6 Hz), 3.45 (2H, m), 3.65 (2H, s), 6.25 (1H, d, J=15 Hz), 6.90 (1H, m), 6.95 (1H, d, J=2 Hz), 7.05 (1H, dd, J=8, 2 Hz), 7.20 (1H, d, J=8 Hz), 7.40 (2H, d, J=8 Hz), 7.55 (1H, d, J=15 Hz), 7.90 (2H, d, J=8 Hz).

(r) (E)-2-(4-(3-(3-Methoxyphenyl)propenoyl)aminobutyl-7-trifluoromethylsulfonyloxy-1,2,3,4-tetrahydroisoquinoline Mass spectrum (API$^+$): Found 513 (MH$^+$). $C_{24}H_{27}F_3N_2O_5S$ requires 512. $^1$H NMR (CDCl$_3$)δ: 1.70 (4H, m), 2.55 (2H, m), 2.75 (2H, t, J=6 Hz), 2.95 (2H, t, J=6 Hz), 3.45 (2H, m), 3.65 (2H, s), 3.80 (3H, s), 6.20 (1H, d, J=15 Hz), 6.55(1H, m), 6.90 (1H, m), 7.05 (1H, dd, J=8, 2 Hz), 7.20 (2H, m), 7.55 (1H, d, J=15 Hz).

(s) (E)-2-(4-(3-(3-Quinolinyl)propenoyl)aminobutyl-7-trifluoromethylsulfonyloxy-1,2,3,4-tetrahydroisoquinoline Mass spectrum (API$^+$): Found 534 (MH$^+$). $C_{26}H_{26}F_3N_3O_4S$ requires 533. $^1$H NMR (CDCl$_3$)δ: 1.75 (4H, m), 2.60 (2H, m), 2.75 (2H, t, J=6 Hz), 2.95 (2H, t, J=6 Hz), 3.50 (2H, m), 3.65 (2H, s), 6.45 (1H, d, J=15 Hz), 6.65 (1H, m), 6.95 (1H, d, J=2 Hz), 7.00 (1H, dd, J=8, 2 Hz), 7.15 (1H, d, J=8 Hz), 7.55 (1H, m), 7.75 (3H, m), 8.10 (2H, m), 9.00 (1H, d, J=2 Hz).

(t) (E)-2-(4-(3-(5-(2,3-Dihydro)benzofuranyl)propenoyl)aminobutyl-7-trifluoromethylsulfonyloxy-1,2,3,4-tetrahydroisoquinoline Mass spectrum (API$^+$): Found 525 (MH$^+$). $C_{25}H_{27}F_3N_2O_5S$ requires 524. $^1$H NMR (CDCl$_3$)δ: 1.70 (4H, m), 2.60 (2H, m), 2.75 (2H, t, J=6 Hz), 2.95 (2H, t, J=6 Hz), 3.20 (2H, t, J=8 Hz), 3.40 (2H, m), 3.65 (2H, s), 4.60 (2H, t, J=8 Hz), 6.05 (1H, d, J=15 Hz), 6.40 (1H, m), 6.75 (1H, d, J=7 Hz), 6.95 (1H, d, J=2 Hz), 7.05 (1H, dd, J=8, 2 Hz), 7.20 (2H, m), 7.25 (1H, d, J=7 Hz), 7.50(1H, d, J=15 Hz).

(u) (E)-2-(4-(3-(6-(1,4-benzodioxanyl))propenoyl)aminobutyl-7-trifluoromethylsulfonyloxy-1,2,3,4-tetrahydroisoquinoline Mass spectrum (API$^+$): Found 541 (MH$^+$). $C_{25}H_{27}F_3N_2O_6S$ requires 540. $^1$H NMR (CDCl$_3$) δ: 1.70 (4H, m), 2.60 (2H, m), 2.75 (2H, t, J=6 Hz), 2.95 (2H, t, J=6 Hz), 3.40 (2H, m), 3.65 (2H, s), 4.30 (4H, s), 6.00 (1H, d, J=15 Hz), 6.65 (1H, m), 6.85 (3H, m), 6.95 (1H, d, J=2 Hz), 7.05 (1H, dd, J=8, 2 Hz), 7.20 (1H, d, J=8 Hz), 7.45 (1H, d, J=15 Hz).

(v) (E)-2-(4-(3-(3-Acetylphenyl)propenoyl)aminobutyl)-7-trifluoromethylsulfonyloxy-1,2,3,4-tetrahydroisoquinoline Mass spectrum (API$^+$): Found 525 (MH$^+$). $C_{25}H_{27}F_3N_2O_5S$ requires 524. $^1$H NMR (CDCl$_3$) δ: 1.70 (4H, m), 2.55 (2H, m), 2.60 (3H, s), 2.75 (2H, t, J=7 Hz), 2.95 (2H, t, J=7 Hz), 3.45 (2H, m), 3.65 (2H, s), 6.30 (1H, d, J=15 Hz), 6.65 (1 h, m), 6.95 (1H, d, J=2 Hz), 7.00 (1H, dd, J=8, 2 Hz), 7.20 (1H, d, J=8 Hz), 7.45 (2H, m), 7.60 (1H, d, J=15 Hz), 7.90 (1H, d, J=7 Hz), 8.0 (1H, br s).

(w) (E)-2-(4-(3-(3-Acetamidophenyl)propenoyl)aminobutyl)-7-trifluoromethylsulfonyloxy-1,2,3,4-tetrahydroisoquinoline Mass spectrum (API$^+$): Found 540 (MH$^+$). $C_{25}H_{28}F_3N_3O_5S$ requires 539. $^1$H NMR (CDCl$_3$)δ: 1.75 (4H, m), 2.20 (3H, s), 2.55 (2H, m), 2.75 (2H, t, J=6 Hz), 2.90 (2H, t, J=6 Hz), 3.40 (2H, m), 3.65 (2H, s), 6.25 (1H, d, J=15 Hz), 6.65 (1H, m), 6.95 (1H, d, J=2 Hz), 7.05 (2H, m), 7.15 (1H, d, J=8 Hz), 7.25 (1H, m), 7.45 (1H, br d, J=8 Hz), 7.50 (1H, d, J=15 Hz), 7.65 (2H, m).

(x) (E)-2-(4-(3-(3-Dimethylaminophenyl)propenoyl)aminobutyl)-7-trifluoromethylsulfonyloxy-1,2,3,4-tetrahydroisoquinoline Mass spectrum (API$^+$): Found 526 (MH$^+$). $C_{25}H_{30}F_3N_3O_4S$ requires 525. $^1$H NMR (CDCl$_3$)δ: 1.70 (4H, m), 2.55 (2H, m), 2.75 (2H, t, J=6 Hz), 2.90 (2H, m), 2.95 (6H, s), 3.45 (2H, m), 3.65 (2H, s), 6.20 (1H, d, J=15 Hz), 6.40 (1H, m), 6.75 (3H, m), 6.95 (1H, d, J=2 Hz), 7.05 (1H, dd, J=8, 2 Hz), 7.20 (2H, m), 7.55 (1H, d, J=15 Hz).

(y) (E)-2-(4-(3-(2-Quinoxalinyl)propenoyl)aminobutyl)-7-trifluoromethylsulfonyloxy-1,2,3,4-tetrahydroisoquinoline Mass spectrum (API$^+$): Found 535 (MH$^+$). $C_{25}H_{25}F_3N_4O_4S$ requires 534. $^1$H NMR (CDCl$_3$) δ: 1.70 (4H, m), 2.60 (2H, m), 2.75 (2H, t, J=6 Hz), 2.95 (2H, t, J=6 Hz), 3.50 (2H, m), 3.65 (2H, s), 6.70 (1H, m), 7.00 (2H, m), 7.05 (1H, d, J=15 Hz), 7.15 (1H, m), 7.75 (3H, m), 8.10 (2H, m), 8.95 (1H, s).

(z) (E)-2-(4-(3-(2-Benzothiazolyl)propenoyl)aminobutyl)-7-trifluoromethylsulfonyloxy-1,2,3,4-tetrahydroisoquinoline Mass spectrum (API$^+$): Found 540 (MH$^+$). $C_{24}H_{24}F_3N_3O_4S_2$ requires 539. $^1$H NMR (CDCl$_3$)δ: 1.70 (4H, m), 2.60 (2H, m), 2.75 (2H, t, J=6 Hz), 2.95 (2H, t, J=6 Hz), 3.45 (2H, m), 3.65 (2H, s), 6.65 (1H, d, J=15 Hz), 6.95 (3H, m), 7.15 (1H, d, J=8 Hz), 7.45 (2H, m), 7.75 (1H, d, J=15 Hz), 7.85 (1H, d, J=8 Hz), 8.05 (1H, d, J=8 Hz).

(a1) (E)-2-(4-(3-(3,4-Dichlorophenyl)propenoyl)aminobutyl)-7-trifluoromethylsulfonyloxy-1,2,3,4-tetrahydroisoquinoline Mass spectrum (API$^+$): Found 551 (MH$^+$). $C_{23}H_{23}{}^{35}Cl_2F_3N_2O_4S$ requires 550. $^1$H NMR (CDCl$_3$) δ: 1.70 (4H, m), 2.60 (2H, m), 2.75 (2H, t, J=6 Hz), 2.95 (2H, t, J=6 Hz), 3.40 (2H, m), 3.65 (2H, s), 6.15 (1H, d, J=15 Hz), 6.75 (1H, m), 6.95 (1H, d, J=2 Hz), 7.05 (1H, dd, J=8, 2 Hz), 7.15 (2H, m), 7.40 (3H, m).

(b1) (E)-2-(4-(3-(2-(1-Methyl)pyrrolyl)propenoyl)aminobutyl)-7-trifluoromethylsulfonyloxy-1,2,3,4-tetrahydroisoquinoline Mass spectrum (API$^+$): Found 486 (MH$^+$). $C_{22}H_{26}F_3N_3O_4S$ requires 485. $^1$H NMR (CDCl$_3$)δ: 1.70 (4H, m), 2.55 (2H, m), 2.75 (2H, t, J=6 Hz), 2.95 (2H, t, J=6 Hz), 3.40 (2H, m), 3.65 (5H, 2xs), 5.95 (1H, d, J=15 Hz), 6.15 (1H, t, J=3 Hz), 6.30 (1H, m), 6.50 (1H, m), 6.70 (1H, br s), 6.95 (1H, d, J=2 Hz), 7.05 (1H, dd, J=8, 2 Hz), 7.20 (1H, d, J=8 Hz), 7.55 (1H, d, J=15 Hz).

(c1) (E)-2-(4-(3-(5-Pyrido[2,3-b]indolyl)propenoyl)aminobutyl-7-trifluoromethylsulfonyloxy-1,2,3,4-tetrahydroisoquinoline Mass spectrum (API$^+$): Found 523 (MH$^+$). $C_{24}H_{25}F_3N_4O_4S$ requires 522. $^1$H NMR (CDCl$_3$) δ: 1.70 (4H, m), 2.60 (2H, m), 2.80 (2H, t, J=6 Hz), 3.00 (2H, m), 3.40 (2H, m), 3.60 (2H, m), 6.40 (1H, d, J=15 Hz), 6.90 (1H, br s), 7.05 (1H, m), 7.20 (2H, m), 7.55 (1H, m), 7.70 (1H, d, J=15 Hz), 7.90 (1H, m), 8.25 (3H, m).

(d1) (E)-2-(4-(3-(5-(2-Dimethylamino)pyrimidyl)propenoyl)aminobutyl)-7-trifluoromethylsulfonyloxy-1,2,3,4-tetrahydroisoquinoline Mass spectrum (API$^+$): Found 528 (MH$^+$). $C_{23}H_{28}F_3N_5O_4S$ requires 527. $^1$H NMR (CDCl$_3$) δ: 1.75 (4H, m), 2.55(2H, m), 2.75 (2H, t, J=6 Hz), 2.95 (2H, t, J=6 Hz), 3.20 (6H, s), 3.40 (2H, m), 3.65 (2H, s), 6.05 (1H, d, J=15 Hz), 6.50 (1H, m), 6.95 (1H, d, J=2 Hz), 7.05 (1H, dd, J=8, 2 Hz), 7.15 (1H, d, J=8 Hz), 7.40 (1H, d, J=15 Hz), 8.30 (2H, s).

(e1) (E)-2-(4-(3-(2-Benzoxazolyl)propenoyl)aminobutyl)-7-trifluoromethylsulfonyloxy-1,2,3,4-tetrahydroisoquinoline Mass spectrum (API$^+$): Found 524 (MH$^+$). $C_{24}H_{24}F_3N_3O_5S$ requires 523. $^1$H NMR (CDCl$_3$) δ: 1.75

(4H, m), 2.60 (2H, m), 2.75 (2H, t, J=6 Hz), 2.95 (2H, t, J=6 Hz), 3.40 (2H, m), 3.65 (2H, s), 6.80 (1H, d, J=15 Hz), 6.85 (1H, m), 6.95 (2H, m), 7.15 (1H, d, J=8 Hz), 7.35 (2H, m), 7.45 (1H, d, J=15 Hz), 7.50 (1H, m), 7.75 (1H, m).

(f1) (E)-2-(4-(3-(4-(1-Pyrrolidinyl)phenyl)propenoyl)aminobutyl)-7-trifluoromethylsulfonyloxy-1,2,3,4-tetrahydroisoquinoline Mass spectrum (API$^+$): Found 552 (MH$^+$). C$_{17}$H$_{12}$F$_3$N$_3$O$_4$S requires 551. $^1$H NMR (CDCl$_3$) δ: 1.70 (4H, m), 2.05 (4H, m), 2.55 (2H, m), 2.75 (2H, t, J=6 Hz), 2.95 (2H, t, J=6 Hz), 3.30 (4H, m), 3.40 (2H, m), 3.65 (2H, s), 5.95 (1H, d, J=15 Hz), 6.35 (1H, m), 6.50 (2H, d, J=8 Hz), 6.95 (1H, d, J=2 Hz), 7.05 (1H, dd, J=8, 2 Hz), 7.20 (1H, d, J=8 Hz), 7.25 (2H, d, J=8 Hz), 7.50 (1H, d, J=15 Hz).

(g1) (E)-2-(4-(3-(3-Methylaminocarbonylphenyl)propenoyl)aminobutyl)-7-trifluoromethylsulfonyloxy-1,2,3,4-tetrahydroisoquinoline.

Mass spectrum (API$^+$): Found 540(MH$^+$). C$_{25}$H$_{28}$N$_3$F$_3$O$_5$S requires 539. $^1$H NMR (CDCl$_3$) δ: 1.60–1.72 (4H, m), 2.52 (2H, t, J=6 Hz), 2.73 (2H, t, J=6 Hz), 2.92 (2H, t, J -6 Hz), 3.00 (3H, d, J=5 Hz), 3.37–3.48 (2H, m), 3.64 (2K,br s), 6.29 (1H, d, J=13 Hz), 6.49 (1H, m), 6.75 (1H, m), 6.95 (1H, d, J=3 Hz), 7.03 (1H, dd, J=3, 5 Hz), 7.17 (1H, d, J=5 Hz), 7.3–7.49 (2H, m), 7.54 (1H, d, J=13 Hz), 7.69 (1H, m), 7.87 (1H, s).

(h1) (E)-2-(4-(3-(3,4-Methylenedioxyphenyl)propenoyl)aminobutyl)-7-trifluoromethylsulfonyloxy-1,2,3,4-tetrahydroisoquinoline Mass spectrum (API$^+$): Found 527 (MH$^+$). C$_{24}$H$_{25}$N$_2$F$_3$O$_6$S requires 526. $^1$H NMR (CDCl$_3$)δ: 1.55–1.80 (4H, m), 2.55 (2H, t, J=6 Hz), 2.75 (2H, t, J=6 Hz), 2.93 (2H, t, J=6 Hz), 3.44 (2H, m), 3.62 (2H, s), 6.01 (2H, s), 6.22 (1H, d, J=13 Hz), 6.82 (3H, s), 6.95 (1H, d, J=2 Hz), 7.03 (1H, dd, J=2, 7 Hz), 7.15 (1H, d, J=7 Hz), 7.5 (1H, d, J=13 Hz).

(I1) (E)-2-(4-(3-(3-Aminocarbonylphenyl)propenoyl)aminobutyl)-7-trifluoromethylsulfonyloxy-1,2,3,4-tetrahydroisoquinoline Mass spectrum (API$^+$): Found 526 (MH$^+$). C$_{24}$H$_{26}$F$_3$N$_3$O$_5$S requires 525. $^1$H NMR (CDCl$_3$) δ: 1.55–1.79 (4H, m), 2.55 (2H, t, J=5 Hz), 2.75 (2H, t, J=5 Hz), 2.90 (2H, t, J=5 Hz), 3.30–3.45 (2H, m), 3.65 (2H, s), 5.95 (2H, br s), 6.32 (1H, D, J=13 Hz), 6.70 (1H, t, J=6 Hz), 6.95 (1H, d, J=3 Hz), 7.02 (1H, dd, J=3, 6 Hz), 7.16 (1H, d, J=6 Hz), 7.30–7.48 (2H, m), 6.57 (1H, d, J=7 Hz), 7.73 (1H, d, J=5 Hz), 8.90 (1H, s).

(j1) (E)-2-(4-(3-(2-Acetamidophenyl)propenoyl)aminobutyl)-7-trifluoromethylsulfonyloxy-1,2,3,4-tetrahydroisoquinoline Mass spectrum (API$^+$): Found 540 (MH$^+$). C$_{25}$H$_{28}$F$_3$N$_3$O$_5$S requires 539. $^1$H NMR (CDCl$_3$) δ: 1.52–1.70 (4H, m), 2.17 (3H, s), 2.50 (2H, t, J=5 Hz), 2.71 (2H, t, J=5 Hz), 2.90 (2H, t, J=5 Hz), 3.30 (2H, m), 3.60 (2H, s), 6.17 (1H, d, J=13 Hz), 6.92 (1H, d, J=3 Hz), 7.05 (2H, m), 7.15 (1H, d, J=7 Hz), 7.20–7.35 (3H, m), 7.59 (1H, d, J=7 Hz), 7.7 (1H, d, J=13 Hz), 8.58 (1H, s).

(k1) (E)-2-(4-(3-(2-Naphthyl)propenoyl)aminobutyl)-7-(2-thiophene)sulfonyloxy-1,2,3,4-tetrahydroisoquinoline Mass spectrum (API$^+$): Found 547 (MH$^+$). C$_{30}$H$_{30}$N$_2$O$_4$S$_2$ requires 546. $^1$H NMR (CDCl$_3$) δ: 1.70 (4H, m), 2.55 (2H, m), 2.74 (2H, t, J=7 Hz), 2.90 (2H, t, J=7 Hz), 3.43 (2H, m), 3.58 (2H, s), 6.26 (1H, d, J=16 Hz), 6.78 (2H, m), 6.86 (1H, m), 7.05 (2H, m), 7.38 (1H, m), 7.50 (2H, m), 7.56 (1H, m), 7.68 (2H, m), 7.80 (4H, m).

(l1) (E)-2-(4-(3-(4-Dimethylaminophenyl)propenoyl)aminobutyl)-7-(2-thiophene)sulfonyloxy-1,2,3,4-tetrahydroisoquinoline Mass spectrum (API$^+$): Found 540 (MH$^+$). C$_{28}$H$_{33}$N$_3$O$_4$S$_2$ requires 539. $^1$H NMR (CDCl$_3$) δ: 1.68 (4H, m), 2.55 (2H, m), 2.74 (2H, t, J=7 Hz), 2.90 (2H, t, J=7 Hz), 3.00 (6H, s), 3.40 (2H, m), 3.55 (2H, s), 5.95 (1H, d, J=13 Hz), 6.64 (3H, m), 6.74 (1H, d, J=3 Hz), 6.80 (1H, dd, J=10, 3 Hz), 7.05 (2H, m), 7.24 (2H, d, J=10 Hz), 7.50 (1H, d, J=13 Hz), 7.58 (1H, dd, J=7, 3 Hz), 7.70 (1H, dd, J=7, 3 Hz).

(m1) (E)-2-(4-(3-(2-Naphthyl)propenoyl)aminobutyl-7-methylsulfonyloxy-1,2,3,4-tetrahydroisoquinoline Mass spectrum (API$^+$): Found 479 (MH$^+$). C$_{27}$H$_{30}$N$_2$O$_4$S requires 478. $^1$H NMR (CDCl$_3$) δ: 1.70 (4H, m), 2.58 (2H, m), 2.75 (2H, t, J=7 Hz), 2.95 (2H, t, J=7 Hz), 3.08 (3H, s), 3.45 (2H, m), 3.66 (2H, s), 6.28 (1H, d, J=16 Hz), 6.90 (1H, m), 7.00 (1H, d, J=3 Hz), 7.06 (1H, dd, J=10, 3 Hz), 7.15 (1H, d, J=10 Hz), 7.36 (1H, m), 7.50 (2H, m), 7.74 (1H, d, J=16 Hz), 7.82 (4H, m).

(n1) (E)-2-(4-(3-(4-Dimethylaminophenyl)propenoyl)aminobutyl)-7-methylsulfonyloxy-1,2,3,4-tetrahydroisoquinoline Mass spectrum (API$^+$): Found 472 (MH$^+$). C$_{25}$H$_{33}$N$_3$O$_4$S requires 471. $^1$H NMR (CDCl$_3$) δ: 1.70 (4H, m), 2.55 (2H, m), 2.75 (2H, t, J=7 Hz), 2.95 (8H, m), 3.40 (2H, m), 3.64 (2H, s), 5.96 (1H, d, J=16 Hz), 6.64 (3H, m), 7.00 (1H, d, J=3 Hz), 7.02–7.30 (4H, m), 7.52 (1H, d, J=16 Hz).

(o1) (E)-2-(4-(3-(2-Naphthyl)propenoyl)aminobutyl)-7-acetyl-1,2,3,4-tetrahydroisoquinoline Mass spectrum (API$^+$): Found 427 (MH$^+$). C$_{28}$H$_{30}$N$_2$O$_2$ requires 426. $^1$H NMR (CDCl$_3$)δ: 1.75 (4H, m), 2.50 (3H, s), 2.62 (2H, m), 2.75 (2H, t, J=5 Hz), 3.00 (2H, t, J=5 Hz), 3.45 (2H, m), 3.72 (2H, s), 6.24 (1H, d, J=13 Hz), 7.16–7.32 (3H, m), 7.48 (2H, m), 7.67 (2H, s), 7.70–7.84 (5H, m).

(p1) (E)-2-(4-(3-(2-Naphthyl)propenoyl)aminobutyl)-7-bromo-1,2,3,4-tetrahydroisoquinoline Mass spectrum (API$^+$): Found 463 (MH$^+$). C$_{26}$H$_{27}$$^{79}$BrN$_2$O requires 462. $^1$H NMR (CDCl$_3$) δ: 1.75 (4H, m), 2.57 (2H, t, J=5 Hz), 2.75 (2H, t, J=5 Hz), 2.90 (2H, t, J=5 Hz), 3.45 (2H, m), 3.65 (2H, s), 6.18 (1H, d, J=15 Hz), 7.00 (1H, d, J=8 Hz), 7.14–7.73 (3H, m), 7.45 (3H, m), 7.64–7.90 (5H, m).

(q1)(E)-2-(4-(3-(2-Naphthyl)propenoyl)aminobutyl)-7-(4-cyanophenyl)sulfonyloxy-1,2,3,4-tetrahydroisoquinoline Mass spectrum (API$^+$): Found 566 (MH$^+$). C$_{33}$H$_{31}$N$_3$O$_4$S requires 565. $^1$H NMR (CDCl$_3$) δ: 1.70 (4H, m), 2.55 (2H, t, J=5 Hz), 2.75 (2H, t, J=5 Hz), 2.92 (2H, t, J=5 Hz), 3.45 (2H, m), 3.55 (2H, s), 6.30 (1H, d, J=15 Hz), 6.72 (3H, m), 7.04 (1H, d, J=8 Hz), 7.40 (1H, m), 7.45–7.55 (2H, m), 7.68–8.00 (9H, m).

(r1) (E)-2-(4-(3-(2-Naphthyl)propenoyl)aminobutyl)-7-methoxy-1,2,3,4-tetrahydroisoquinoline Mass spectrum (API$^+$): Found 415 (MH$^+$). C$_{27}$H$_{30}$N$_2$O$_2$ requires 414. $^1$H NMR (CDCl$_3$) δ: 1.75 (4H, m), 2.58 (2H, t, J=7 Hz), 2.75 (2H, t, J=7 Hz), 2.90 (2H, t, J=7 Hz), 3.43 (2H, m), 3.67 (2H, s), 3.74 (3H, s), 6.14 (1H, d, J=17 Hz), 6.62 (1H, d, J=3 Hz), 6.76 (1H, dd, J=3, 10 Hz), 7.05 (1H, d, J=10 Hz), 7.15 (1H, dd, J=3, 10 Hz), 7.47 (2H, m), 7.66 (1H, d, J=10 Hz), 7.74 (2H, s), 7.80 (2H, m), 8.00 (1H, m).

(s1) (E)-7-Phenylsulfonylmethyl-2-(4-(3-(2-naphthyl)propenoyl)aminobutyl)-1,2,3,4-tetrahydroisoquinoline Mass spectrum (API$^+$): Found 539 (MH$^+$). C$_{33}$H$_{34}$N$_2$O$_3$S requires 538. $^1$H NMR (CDCl$_3$) δ: 1.70 (4H, m), 2.54 (2H, m), 2.73 (2H, t, J=7 Hz), 2.91 (2H, t, J=7 Hz), 3.44 (2H, m), 3.53 (2H, s), 4.16 (2H, s), 6.29 (1H, d, J=15 Hz), 6.75 (1H, d, J=2 Hz), 6.85 (1H, dd, J=9, 2 Hz), 6.99 (1H, br s), 7.00 (1H, d, J=9 Hz), 7.35–7.88 (13H, m).

(t1) (E)-7-Methylsulfonamido-2-(4-(3-(2-naphthyl)propenyl)aminobutyl)-1,2,3,4-tetrahydroisoquinoline Mass spectrum (API⁺): Found 478 (MH⁺). $C_{27}H_{31}N_3O_3S$ requires 477. ¹H NMR (CDCl₃) δ: 1.72 (4H, m), 2.55 (2H, m), 2.75 (2H, t, J=10 Hz), 2.91 (5H, m), 3.44 (2H, m), 3.61 (2H, s), 6.21 (1H, d, J=15 Hz), 6.91 (1H, d, J=2 Hz), 7.00 (1H, dd, J=8, 2 Hz), 7.10 (1H, d, J=8 Hz), 7.32 (1H, dd, J=8, 2 Hz), 7.46–7.55 (3H, m), 7.70 (1H, d, J=15 Hz), 7.78–7.86 (5H, m).

(u1) (E)-2-(4-(3-(2-Naphthyl)propenoyl)aminobutyl)-7-phenylsulfonamido-1,2,3,4-tetrahydroisoquinoline Mass spectrum (API⁺): Found 540 (MH⁺). $C_{32}H_{33}N_3O_3S$ requires 539. ¹H NMR (CDCl₃) δ: 1.65 (4H, m), 2.49 (2H, m), 2.71 (2H, m), 2.81 (2H, m), 3.40 (2H, m), 3.49 (2H, s), 6.28 (1H, d, J=15 Hz), 6.71 (1H, d, J=2 Hz), 6.90 (2H, m), 7.19 (1H, m), 7.29–7.51 (6H, m), 7.69–7.82 (8H, m).

(v1) (E)-7-(4-Cyanophenyl)sulfonamido-2-(4-(3-(2-naphthyl)propenoyl)aminobutyl-1,2,3,4-tetrahydroisoquinoline Mass spectrum (API⁺): Found 565 (MH⁺). $C_{33}H_{32}N_4O_3S$, requires 564. ¹H NMR (CDCl₃) δ: 1.58 (4H, m), 2.34 (2H, m), 2.64 (2H, m), 2.76 (2H, m), 3.88 (4H, m), 6.21 (1H, d, J=16 Hz), 6.72 (1H, s), 6.88–7.04 (2H, m), 7.18 (1H, d, J=10 Hz), 7.40–7.51 (4H, m), 7.58 (2H, d, J=9 Hz), 7.66–7.89 (7H, m).

(w1) (E)-2-(4-(3-(5-Indolyl)propenoyl)aminobutyl)-7-trifluoromethylsulfonyloxy-1,2,3,4-tetrahydroisoquinoline Mass spectrum (API⁺): Found 522 (MH⁺). $C_{25}H_{26}F_3N_3O_4S$ requires 521. ¹H NMR (CDCl₃) δ: 1.70 (4H, m), 2.55 (2H, t, J=6 Hz), 2.75 (2H, t, J=6 Hz), 2.90 (2H, t, J=6 Hz), 3.45 (2H, m), 3.65 (2H, s), 6.20 (1H, d, J=16 Hz), 6.45 (1H, m), 6.55 (1H, m), 6.95 (1H, d, J=2 Hz), 7.05 (1H, dd, J=8,2 Hz), 7.15 (1H, d, J=8 Hz), 7.20–7.30 (2H, m), 7.35 (1H, d, J=8 Hz), 7.65 (1H, s), 7.70 (1H, d, J=16 Hz), 8.50 (1H, br s).

(x1) (E)-2-(4-(3-(5-Benzimidazolyl)propenoyl)aminobutyl)-7-trifluoromethylsulfonyloxy-1,2,3,4-tetrahydroisoquinoline Mass spectrum (API⁺): Found 523 (MH⁺). $C_{24}H_{25}F_3N_4O_4S$ requires 522. ¹H NMR (CD₃OD): δ: 1.50 (4H, m), 2.45 (2H, t, J=7 Hz), 2.65 (2H, t, J=6 Hz), 2.75 (2H, t, J=6 Hz), 3.20 (2H, m), 3.50 (2H, s), 6.40 (1H, d, J=16 Hz), 6.90 (2H, m), 7.10 (1H, d, J=8 Hz), 7.35 (1H, dd, J=8, 2 Hz), 7.45 (1H, d, J=8 Hz), 7.50 (1H, d, J=16 Hz), 7.60 (1H, s), 8.05 (1H, s).

(y1) (E)-7-Methylsulfonylmethyl-2-(4-(3-(2-naphthyl)propenoyl)aminobutyl)-1,2,3,4-tetrahydroisoquinoline Mass spectrum (API⁺): Found 477 (MH⁺). $C_{28}H_{32}N_2O_3S$ requires 476. ¹H NMR (CDCl₃) δ: 1.74 (4H, m), 2.58 (2H, m), 2.70 (3H, s), 2.77 (2H, t, J=7 Hz), 2.96 (2H, t, J=7 Hz), 3.44 (2H, m), 3.66 (2H, s), 4.10 (2H, s), 6.29 (1H, d, J=15 Hz), 6.95 (1H, m), 7.08 (1H, s), 7.16 (2H, s), 7.39 (1H, dd, J=9, 2 Hz), 7.50 (2H, m), 7.65–7.87 (5H, m).

(z1) (E)-2-(4-((2-Naphthyl)propenoyl)aminobutyl)-7-trifluoromethoxy-1,2,3,4-tetrahydroisoquinoline Mass spectrum (API⁺): Found 469 (MH⁺). $C_{27}H_{27}F_3N_2O_2$ requires 468. ¹H NMR (CDCl₃) δ: 1.72 (4H, m), 2.57 (2H, t, J=6 Hz), 2.75 (2H, t, J=6 Hz), 2.91 (2H, t, J=6 Hz), 3.45 (2H, m), 3.65 (2H, s), 6.26 (1H, d, J=16 Hz), 6.94 (1H, s), 6.96–7.17 (3H, m), 7.33 (1H, dd, J=9, 2 Hz), 7.49 (2H, m), 7.73 (1H, d, J=9 Hz), 7.75–7.87 (4H, m).

(a2) (E)-7-Cyano-2-(4-(3-(2-naphthyl)propenoyl)aminobutyl)-1,2,3,4-tetrahydroisoquinoline Mass spectrum (API⁺): Found 410 (MH⁺). $C_{27}H_{27}N_3O$ requires 409. ¹H NMR (CDCl₃) δ: 1.69 (4H, m), 2.56 (2H, m), 2.75 (2H, t, J=7 Hz), 2.97 (2H, t, J=7 Hz), 3.45 (2H, m), 3.64 (2H, s), 6.27 (1H, d, J=16 Hz), 6.80 (1H, d, J=9 Hz), 7.30–7.45 (3H, m), 7.49 (2H, m), 7.75 (1H, d, J=16 Hz), 7.76–7.87 (4H, m).

(b2) (E)-2-(4-(3-(3-Indolyl)propenoyl)aminobutyl)-7-trifluoromethoxy-1,2,3,4-tetrahydroisoquinoline Mass spectrum (API⁺): Found 458 (MH⁺). $C_{25}H_{26}F_3N_3O_2$ requires 457. ¹H NMR (CDCl₃) δ: 1.68 (4H, m), 2.56 (2H, m), 2.73 (2H, t, J=7 Hz), 2.90 (2H, t, J=7 Hz), 3.45 (2H, m), 3.61 (2H, s), 6.26–6.37 (2H, m), 6.90 (1H, br s), 6.98 (1H, m), 7.09 (1H, d, J=8 Hz), 7.15–7.28 (2H, m), 7.33 (1H, d, J=3 Hz), 7.41 (1H, dd, J=8, 2 Hz), 7.77–7.89 (2H, m), 8.82 (1H, br s).

(c2) (E)-2-(4-(3-(4-Dimethylaminophenyl)propenoyl)-7-trifluoromethoxy-1,2,3,4-tetrahydroisoquinoline Mass spectrum (API⁺): Found 462 (MH⁺). $C_{25}H_{30}F_3N_3O_2$ requires 461. ¹H NMR (CDCl₃) δ: 1.70 (4H, m), 2.67 (2H, m), 2.75 (2H, t, J=7 Hz), 2.94 (2H, t, J=7 Hz), 2.99 (6H, s), 3.41 (2H, m), 3.65 (2H, s), 5.95 (1H, d, J=16 Hz), 6.64 (2H, d, J=9 Hz), 6.77 (1H, m), 6.93 (1H, br s), 7.03 (1H, m), 7.14 (1H, d, J=9 Hz), 7.21 (2H, d, J=9 Hz), 7.50 (1H, d, J=16 Hz).

(d2) (E)-7-Cyano-2-(4-(3-(3-indolyl)propenoyl)aminobutyl)-1,2,3,4-tetrahydroisoquinoline Mass spectrum (API⁺): Found 399 (MH⁺). $C_{25}H_{26}N_4O$ requires 398. ¹H NMR (CDCl₃) δ: 1.70 (4H, m), 2.55 (2H, m), 2.70 (2H, t, J=6 Hz), 2.95 (2H, t, J=6 Hz), 3.45 (2H, m), 3.60 (2H, s), 6.25 (1H, m), 6.30 (1 H, d, J=16 Hz), 7.05–7.45 (7H, m), 7.80 (1H, m), 7.85 (1H, d, J=16 Hz), 8.90 (1H, br s).

(e2) (E)-2-(4-(3-(3-(7-Methyl)indolyl)propenoyl)aminobutyl)-7-trifluoromethylsulfonyloxy-1,2,3,4-tetrahydroisoquinoline Mass spectrum (API⁺): Found 536 (MH⁺). $C_{26}H_{28}F_3N_3O_4S$ requires 535. ¹H NMR (CDCl₃) δ: 1.60 (4H, m), 2.45 (2H, m), 2.50 (3H, s), 2.60 (2H, t, J=5 Hz), 2.80 (2H, t, J=5 Hz), 3.40 (2H, m), 3.50 (2H, s), 6.40 (1H, d, J=16 Hz), 6.65 (1H, t, J=5 Hz), 6.85 (1H, d, J=2 Hz), 6.9–7.15 (4H, m), 7.30 (1H, m), 7.65 (1H, d, J=8 Hz), 7.85 (1H, d, J=16 Hz), 9.70 (1H, br s).

(f2) (E)-2-(4-(3-(2-(6-Acetyl)naphthyl)propenoyl)aminobutyl)-7-trifluoromethylsulfonyloxy-1,2,3,4-tetrahydroisoquinoline Mass spectrum (API⁺): Found 575 (MH⁺). $C_{29}H_{29}F_3N_2O_5S$ requires 574. ¹H NMR (CDCl₃) δ: 1.70 (4H, m), 2.60 (2H, m), 2.70 (3H, s), 2.75 (2H, m), 2.95 (2H, m), 3.45 (2H, m), 3.65 (2H, s), 6.35 (1H, d, J=16 Hz), 6.80 (1H, m), 6.95 (1H, d, J=2 Hz), 7.05 (1H, dd, J=8, 2 Hz), 7.20 (1H, d, J=8 Hz), 7.45 (1H, d, J=8 Hz), 7.75 (1H, d, J=16 Hz), 7.85 (3H, m), 8.05 (1H, d, J=9 Hz), 8.40 (1H, s).

(g2) (E)-7-Cyano-2-(4-(3-(3-(7-methyl)indolyl)propenoyl)aminobutyl)-1,2,3,4-tetrahydroisoquinoline Mass spectrum (API⁺): Found 413 (MH⁺). $C_{26}H_{28}N_4O$ requires 412. ¹H NMR (CDCl₃) δ: 1.65 (4H, m), 2.45 (3H, s), 2.50 (2H, m), 2.70 (2H, t, J=6 Hz), 2.95 (2H, t, J=6 Hz), 3.45 (2H, m), 3.55 (2H, s), 6.25 (1H, m), 6.30 (1K, d, J=16 Hz), 7.10 (3H, m), 7.25 (1H, m), 7.40 (2H, m), 7.65 (1H, d, J=8 Hz), 7.85 (1H, d, J=16 Hz), 8.80 (1H, br s).

(h2) (E)-7-Cyano-2-(4-(3-(5-benzimidazolyl)propenoyl)aminobutyl)-2,3,4-tetrahydroisoquinoline Mass spectrum (API⁺): Found 400 (MH⁺). $C_{24}H_{25}N_5O$ requires 399. ¹H NMR (CDCl₃) δ: 1.70 (4H, m), 2.55 (2H, m), 2.75 (2H, m), 2.95 (2H, m), 3.45 (2H, m), 3.60 (2H, s), 6.20 (1H, d, J=16 Hz), 7.15 (3H, m), 7.25 (2H, m), 7.35 (1H, m), 7.60 (2H, m), 7.65 (1H, d, 316 Hz), 8.10 (1H, s).

(i2) (E)-7-Cyano-2-(4-(3-(5-indolyl)propenoyl)aminobutyl)-1,2,3,4-tetrahydroisoquinoline Mass spectrum (API⁺): Found 399 (MH⁺). $C_{25}H_{26}N_4O$ requires 398. ¹H NMR (CDCl₃) δ: 1.70 (4H, m), 2.55 (2H, m), 2.65 (2H, t, J=6 Hz), 2.95 (2H, t, J=6 Hz), 3.45 (2H, m), 3.65 (2H, s), 6.15 (1H, d, J=16 Hz), 6.55 (1H, br s), 6.70 (1 h, m), 7.20 (3H, m), 7.35 (3H, m), 7.65 (1H, s), 7.70 (1H, d, J=16 Hz), 8.55 (1H, br s).

(j2) (E)-2-(4-(3-(2-(6-Acetyl)naphthyl)propenoyl) aminobutyl)-7-cyano-1,2,3,4-tetrahydroisoquinoline Mass spectrum (API$^+$): Found 452 (MH$^+$). $C_{29}H_{29}N_3O_2$ requires 451. $^1$H NMR (CDCl$_3$) δ: 1.70 (4H, m), 2.60 (2H, m), 2.75 (3H, s), 2.80 (2H, m), 2.95 (2H, m), 3.45 (2H, m), 3.65 (2H, s), 6.30 (1H, d, J=16 Hz), 6.95 (1H, m), 7.15–7.50 (4H, m), 7.75 (1H, d, J=16 Hz), 7.85 (3H, m), 8.05 (1H, m), 8.45 (1H, br s).

(k2) (E)-7-Cyano-2-(4-(3-(6-indolyl)propenoyl) aminobutyl)-1,2,3,4-tetrahydroisoquinoline Mass spectrum (API$^+$): Found 399 (MH$^+$). $C_{25}H_{26}N_4O$ requires 398. $^1$H NMR (CDCl$_3$) δ: 1.75 (4H, m), 2.60 (2H, t, J=6 Hz), 2.80 (2H, t, J=6 Hz), 3.00 (2H, t, J=6 Hz), 3.45 (2H m), 3.65 (2H, s), 6.10 (1H, d, J=16 Hz), 6.55 (1H, m), 6.75 (1H, m), 7.10 (1H, dd, J=8.2 Hz), 7.15 (1H, d, J=8 Hz), 7.25 (1H, m), 7.35 (2H, m), 7.40 (1H, br s), 7.60 (1H, d, J=8 Hz), 7.70 (1H, d, J=16 Hz), 8.70 (1H, br s).

(l2) (E)-7-Cyano-2-(4-(3-(3-(7-fluoro)indolyl)propenoyl) aminobutyl)-1,2,3,4-tetrahydroisoquinoline Mass spectrum (API$^+$): Found 417 (MH$^+$). $C_{25}H_{25}FN_4O$ requires 416. $^1$H NMR (CDCl$_3$) δ: 1.70 (4H, m), 2.55 (2H, m), 2.75 (2H, t, J=6 Hz), 2.95 (2H, t, J=6 Hz), 3.45 (2H, m), 3.60 (2H, s), 6.25 (1H, m), 6.30 (1H, d, J=16 Hz), 6.95 (1H, m), 7.10 (2H, m), 7.25 (1H, m), 7.35 (2H, m), 7.55 (1H, d, J=8 Hz), 7.75 (1H, d, J=16 Hz), 9.10 (1H, br s).

(m2) (E)-2-(4-(3-(3-(7-Bromo)indolyl)propenoyl) aminobutyl)-7-trifluoromethoxy-1,2,3,4-tetrahydroisoquinoline Mass spectrum (API$^+$): Found 536 (MH$^+$). $C_{25}H_{25}^{79}BrF_3N_3O_2$ requires 535. $^1$H NMR (DMSO-d$_6$) δ: 1.70 (4H, m), 2.60 (2H, m), 2.75 (2H, m), 2.95 (2H, m), 3.35 (2H, m), 3.70 (2H, s), 6.70 (1H, d, J=16 Hz), 7.20 (3H, m), 7.35 (1H, d, J=8 Hz), 7.75 (1H, d, J=8 Hz), 7.70 (1H, d, J=16 Hz), 7.95 (1H, s), 8.05 (2H, m)I 11.90 (1H, br s).

(n2) (E)-2-(4-(3-(3-(7-Bromo)indolyl)propenoyl) aminobutyl)-7-cyano-1,2,3,4-tetrahydroisoquinoline Mass spectrum (API$^+$): Found 477 (MH$^+$). $C_{25}H_{25}^{79}BrN_4O$ requires 476. $^1$H NMR (DMSO-d$_6$) δ: 1.70 (4H, m), 2.55 (2H, m), 2.75 (2H, m), 2.95 (2H, m), 3.30 (2H, m), 3.60 (2H, s), 6.65 (1H, d, J=16 Hz), 7.15 (1H, m), 7.35 (1H, d, J=8 Hz), 7.45 (1H, d, J=8 Hz), 7.60 (3H, m), 7.80 (1H, s), 7.95 (2H, m), 11.80 (1H, br s).

(o2) (E)-2-(4-(3-(3-(7-Cyano)indolyl)propenoyl) aminobutyl)-7-cyano-1,2,3,4-tetrahydroisoquinoline Mass spectrum (API$^+$): Found 424 (MH$^+$). $C_{26}H_{25}N_5O$ requires 423. $^1$H NMR (DMSO-d$_6$) δ: 1.65 (4H, m), 2.55 (2H, m), 2.70 (2H, m), 2.95 (2H, m), 3.30 (2H, m), 3.60 (2H, s), 6.75 (1H, t, J=16 Hz), 7.40 (2H, m), 7.65 (3H, m), 7.75 (1H, d, J=8 Hz), 8.00 (2H, m), 8.30 (1H, d, J=8 Hz), 12.50 (1H, br s).

(p2) (E)-7-Cyano-2-(4-(3-(5-(2-methyl)indolyl) propenoyl)aminobutyl)-1,2,3,4-tetrahydroisoquinoline Mass spectrum (API$^+$): Found 413 (MH$^+$). $C_{26}H_{28}N_4O$ requires 412. $^1$H NMR (DMSO-d$_6$) δ: 1.60 (4H, m), 2.45 (3H, s), 2.55 (2H, m), 2.75 (2H, t, J=6 Hz), 2.95 (2H, t, J=6 Hz), 3.25 (2H, m), 3.65 (2H, s), 6.20 (1H, s), 6.55 (1H, d, J=16 Hz), 7.30 (3H, m), 7.45 (1H, d, J=16 Hz), 7.60 (3H, br s), 8.00 (1H, t, J=5 Hz), 11.20 (1H, br s).

(q2) (E)-2-(4-(3-(5-(2-Methyl)indolyl)propenoyl) aminobutyl)-7-trifluoromethoxy-1,2,3,4-tetrahydroisoquinoline Mass spectrum (API$^+$): Found 472 (MH$^+$). $C_{26}H_{28}F_3N_3O_2$ requires 471. $^1$H NMR (DMSO-d$_6$) δ: 1.65 (4H, m), 2.45 (3H, s), 2.55 (2H, m), 2.75 (2H, m), 2.90 (2H, m), 3.30 (2H, m), 3.65 (2H, s), 6.20 (1H, s), 6.55 (1H, d, J=16 Hz), 7.20 (2H, m), 7.30 (3H, m), 7.55 (1H, d, J=16 Hz), 7.65 (1H, br s), 8.05 (1H, m), 11.20 (1H, br s).

(r2) (E)-2-(4-(3-(3-(7-Acetyl)indolyl)propenoyl) aminobutyl)-7-cyano-1,2,3,4-tetrahydroisoquinoline Mass spectrum (API$^+$): Found 441 (MH$^+$). $C_{27}H_{28}N_4O_2$ requires 440. $^1$H NMR (DMSO-d$_6$) δ: 1.60 (4H, m), 2.55 (2H, m), 2.70 (2H, m), 2.75 (3H, s), 2.95 (2H, m), 3.25 (2H, m), 3.65 (2H, s), 6.75 (1H, d, J=16 Hz), 7.35 (2H, m), 7.65 (2H, m), 7.70 (1H, d, J=16 Hz), 7.80 (1H, d, J=2 Hz), 7.90 (1H, m), 8.0 (1H, d, J=7 Hz), 8.25 (1H, d, J=7 Hz), 11.80 (1H, br s).

(s2) (E)-7-Cyano-2-(4-(3-(6-(2-methyl)indolyl) propenoyl)aminobutyl)-1,2,3,4-tetrahydroisoquinoline Mass spectrum (API$^+$): Found 413 (MH$^+$). $C_{26}H_{28}N_4O$ requires 412. $^1$H NMR (DMSO-d$_6$) δ: 1.65 (4H, m), 2.50 (3H, s), 2.60 (2H, m), 2.75 (2H, t, J=6 Hz), 2.95 (2H, t, J=6 Hz), 3.30 (2H, m), 3.65 (2H, s), 6.20 (1H, s), 6.60 (1H, d, J=16 Hz), 7.25 (1H, dd, J=8, 2 Hz), 7.40 (1H, d, J=8 Hz), 7.50 (3H, m), 7.60 (1H, d, J=16 Hz), 7.65 (1H, m), 8.10 (1H, m), 11.20 (1H, br s).

(t2) (E)-7-Cyano-2-(4-(3-(5-(2,3-dihydro-2-oxo)-1H-indolyl)propenoyl)aminobutyl)-1,2,3,4-tetrahydroisoquinoline Mass spectrum (API$^+$): Found 415 (MH$^+$). $C_{25}H_{26}N_4O_2$ requires 414. $^1$H NMR (DMSO-d$_6$) δ: 1.00 (4H, m), 2.70 (2H, m), 2.94 (2H, m), 3.21 (2H, m), 3.36 (2H, s), 3.55 (4H, m), 6.50 (1H, d, J=16 Hz), 6.85 (1H, d, J=9 Hz), 7.25–7.50 (4H, m), 7.56 (2H, m), 8.03 (1H, m), 10.57 (1H, br s).

(u2) (E)-2-(4-(3-(6-(1,2-Dihydro-2-oxo)quinolinyl) propenoyl)aminobutyl)-7-trifluoromethoxy-1,2,3,4-tetrahydroisoquinoline Mass spectrum (API$^+$): Found 486 (MH$^+$). $C_{26}H_{26}F_3N_3O_3$ requires 485. $^1$H NMR (DMSO-d$_6$) δ: 1.65 (4H, m), 2.50 (2H, m), 2.75 (2H, m), 2.90 (2H, m), 3.30 (2H, m), 3.65 (2H, s), 6.60 (1H, d, J=11 Hz), 6.65 (1H, d, J=16 Hz), 7.20 (2H, m), 7.30 (1H, d, J=8 Hz), 7.40 (1H, d, J=8 Hz), 7.50 (1H, d, J=16 Hz), 7.80 (1H, d, J=8 Hz), 7.90 (1H, s), 8.00 (1H, d, J=10 Hz), 8.25 (1H, m), 12.00 (1H br s).

(v2) (E)-2-(4-(3-(5-(2-Acetyl)indolyl)propenoyl) aminobutyl)-7-cyano-1,2,3,4-tetrahydroisoquinoline Mass spectrum (API$^+$): Found 441 (MH$^+$). $C_{27}H_{28}N_4O_2$ requires 440. $^1$H NMR (DMSO-d$_6$) δ: 1.70 (4H, m), 2.60 (2H, m), 2.70 (3H, s), 2.80 (2H, t, J=6 Hz), 3.00 (2H, t, J=6 Hz), 3.35 (2H, m), 3.70 (2H, s), 6.65 (1H, d, J=16 Hz), 7.40 (1H, d, J=8 Hz), 7.55 (1H, d, J=2 Hz), 7.65 (5H, m), 8.00 (1H, s), 8.20 (1H, m), 12.10 (1H, br s).

(w2) (E)-7-Chloro-2-(4-(3-(6-indolyl)propenoyl) aminobutyl)-1,2,3,4-tetrahydroisoquinoline Mass spectrum (API$^+$) Found 408 (MH$^+$). $C_{24}H_{26}^{35}ClN_3O$ requires 407. $^1$H NMR (CDCl$_3$) δ: 1.72 (4H, m), 2.58 (2H, m), 2.75 (2H, m), 2.91 (2H, m), 3.42 (2H, m), 3.66 (2H, s), 6.05 (1H, d, J=15 Hz), 6.54 (1H, m), 7.04 (2H, m), 7.12 (2H, m), 7.27 (2H, m), 7.41 (1H, m), 7.57 (1H, d, J=8 Hz), 7.67 (1H, d, J=15 Hz), 8.38 (1H, m).

(x2) (E)-7-Cyano-2-(4-(3-(5-(3-methyl)indolyl)propenyl) aminobutyl)-1,2,3,4-tetrahydroisoquinoline Mass spectrum (API$^+$): Found 413 (MH$^+$). $C_{26}H_{28}N_4O$ requires 412. $^1$H NMR (CDCl$_3$+DMSO) δ: 1.51 (4H, m), 2.15 (3H, s), 2.41 (2H, m), 2.58 (2H, m), 2.79 (2H, t, J=5.8 Hz), 3.22 (2H, m), 3.47 (2H, s), 6.17 (1H, d, J=15.5 Hz), 6.82 (1H, s), 6.96 (1H, t, J=5.5 Hz), 7.0–7.3 (5H, m), 7.46 (1H, m), 7.52 (1H, d, J=15.5 Hz), 9.66 (1H, s).

(y2) (E)-2-(4-(3-(6-(3-Methyl)indolyl)propenoyl) aminobutyl)-7-trifluoromethoxy-1,2,3,4-tetrahydroisoquinoline Mass spectrum (API⁺): Found 472 (MH⁺). $C_{26}H_{28}N_3F_3O_2$ requires 471. ¹H NMR (CDCl₃) δ: 1.69 (4H, m), 2.31 (3H, s), 2.55 (2H, m), 2.73 (2H, m), 2.91 (2H, m), 3.40 (2H, m), 3.64 (2H, s), 6.14 (1H, d, J=15.5 Hz), 6.9–7.2 (6H, m), 7.29 (1H, s), 7.48 (1H, d, J=8.3 Hz), 7.71 (1H, d, J=15.5 Hz), 8.37 (1H, s).

(z2) (E)-7-Cyano-2-(4-(3-(5-(1-methyl)indolyl) propenoyl)aminobutyl)-1,2,3,4-tetrahydroisoquinoline Mass spectrum (API⁺): Found 413 (MH⁺). $C_{26}H_{28}N_4O$ requires 412. ¹H NMR (CDCl₃) δ: 1.69 (4H, m), 2.58 (2H, m), 2.75 (2H, t, J=6 Hz), 2.97 (2H, m), 3.39 (2H, m), 3.65 (2H, s), 3.81 (3H, s), 6.31 (1H, d, J=15.8 Hz), 6.48 (1H, d, J=3 Hz), 7.08 (1H, d, J=3 Hz), 7.1–7.4 (6H, m), 7.66 (1H, s), 7.67 (1H, d, J=15.8 Hz).

(a3) (E)-2-(4-(3-(2-(1-Methyl)indolyl)propenoyl) aminobutyl)-7-trifluoromethylsulfonyloxy-1,2,3,4-tetrahydroisoquinoline Mass spectrum (API⁺): Found 536 (MH⁺). $C_{26}H_{28}F_3N_3O_4S$ requires 535. ¹H NMR (CDCl₃) δ: 1.65 (4H, m), 2.50 (2H, m), 2.65 (2H, t, J=5 Hz), 2.85 (2H, m), 3.40 (2H, m), 3.55 (2H, s), 3.70 (3H, s), 6.40 (1H, d, J=15 Hz), 6.65 (1H, s), 6.90 (1H, s), 7.05 (3H, m), 7.20 (3H, m), 7.45 (1H, d, J=8 Hz), 7.70 (1H, d, J=15 Hz).

(b3) (E)-2-(4-(3-(5-Indolyl)propenoyl)aminobutyl)-1,2,3,4-tetrahydroisoquinoline Mass spectrum (API⁺): Found 374 (MH⁺). $C_{24}H_{27}N_3O$ requires 373. ¹H NMR (CDCl₃) δ: 1.75 (4H, m), 2.55 (2H, m), 2.75 (2H, t, J=6 Hz), 2.95 (2H, t, J=6 Hz), 3.40 (2H, m), 3.70 (2H, s), 6.05 (1H, d, J=16 Hz), 6.55 (1H, s), 7.05 (1H, m), 7.20 (7H, m), 7.55 (1H, s), 7.65 (1H, d, J=16 Hz), 8.25 (1H, br s).

(c3) (E)-7-Cyano-2-(4-(3-(5-(2-methyl)benzimidazolyl) propenoyl)aminobutyl)-1,2,3,4-tetrahydroisoquinoline Mass spectrum (API⁺): Found 414 (MH⁺). $C_{25}H_{27}N_5O$ requires 413. ¹H NMR (CDCl₃) δ: 1.70 (4H, m), 2.55 (2H, m), 2.60 (3H, s), 2.75 (2H, t, J=6 Hz), 3.00 (2H, t, J=6 Hz), 3.45 (2H, m), 3.65 (2H, s), 6.10 (1H, d, J=16 Hz), 6.90 (1H, br s), 7.20 (2H, m), 7.35 (3H, m), 7.50 (2H, m), 7.70 (1H, d, J=16 Hz).

(d3) (E)-2-(4-(3-(5-(2-Methyl)benzimidazolyl) propenoyl)aminobutyl)-7-trifluoromethoxy-1,2,3,4-tetrahydroisoquinoline Mass spectrum (API⁺): Found 473 (MH⁺). $C_{25}H_{27}F_3N_4O_2$ requires 472. ¹H NMR (CDCl₃) δ: 1.70 (4H, m), 2.55 (2H, t, J=6 Hz), 2.65 (3H, s), 2.75 (2H, t, J=6 Hz), 2.95 (2H, t, J=6 Hz), 3.40 (2H, m), 3.65 (2H, s), 6.10 (1H, d, J=16 Hz), 6.95 (1H, br s), 7.00 (1H, m), 7.10 (2H, m), 7.45 (4H, m), 7.70 (1H, d, J=16 Hz).

(e3) (E)-2-(4-(3-(5-Indolyl)propenoyl)aminobutyl)-7-trifluoromethyl-1,2,3,4-tetrahydroisoquinoline Mass spectrum (API⁺): Found 442 (MH⁺). $C_{25}H_{26}F_3N_3O$ requires 441. ¹H NMR (CDCl₃) δ: 1.72 (4H, m), 2.59 (2H, m), 2.76 (2H, m), 2.16 (2H, m), 3.43 (2H, m), 3.70 (2H, s), 6.61 (1H, d, J=15.5 Hz), 6.56 (1H, s), 6.66 (1H, m), 7.10–7.45 (6H, m), 7.68 (1H, s), 7.71 (1H, d, J=15.5 Hz), 8.31 (1H, br s).

(f3) (E)-2-(4-(3-(5-Indolyl)propenoyl)aminobutyl)-7-methylsulfonamido-1,2,3,4-tetrahydroisoquinoline Mass spectrum (API⁺): Found 467 (MH⁺). $C_{25}H_{30}N_4O_3S$ requires 466. ¹H NMR (HCl salt) (DMSO-d₆) δ: 1.08 (4H, m), 1.50–2.00 (6H, m), 2.85 (3H, d, J=5 Hz), 3.08 (4H, m), 6.55 (1H, s), 6.70 (1H; d, J=15. 7 Hz), 7.10–7.35 (3H, m), 7.40–7.65 (4H, m), 7.84 (1H, s), 9.95 (1H, s), 10.32 (1H, br s), 10.96 (1I, br s), 11.42 (1H, s).

(g3) (E)-2-(4-(3-(5-Indolyl)propenoyl)aminobutyl)-7-methylaminosulfonyl-1,2,3,4-tetrahydroisoquinoline Mass spectrum (API⁺): Found 467 (MH⁺). $C_{25}H_{30}N_4O_3S$ requires 466. ¹H NMR (CD₃OD) δ: 1.60–1.80 (4H, m), 2.48 (3H, s), 2.62 (2H, m), 2.82 (2H, m), 3.00 (2H, m), 3.39 (2H, m), 3.73 (2H, s), 6.45 (1H, s), 6.51 (1H, d, J=17 Hz), 7.25 (1H, d, J=3 Hz), 7.35 (3H, m), 7.63 (3H, m), 7.73 (1H, m), 7.79 (1H, br s).

(h3) (E)-2-(4-(3-(3-(7-Methyl)indolyl)propenoyl) aminobutyl)-7-trifluoromethoxy-1,2,3,4-tetrahydroisoquinoline Mass spectrum (API⁺): Found 472 (MH⁺). $C_{26}H_{28}F_3N_3O_2$ requires 471. ¹H NMR (CDCl₃) δ: 1.66–1.71 (4H, m), 2.51 (3H, s), 2.56 (2H, m), 2.74 (2H, m), 2.93 (2H, m), 3.44 (2H, m), 3.63 (2H, s), 6.23 (1H, m), 6.31 (1H, d, J=15.5 Hz), 6.89 (1H, s), 6.90–7.20 (4H, m), 7.35 (1H, d, J=2.75 Hz), 7.67 (1H, d, J=7.7 Hz), 7.83 (1H, d, J=15.5 Hz), 8.48 (1H, br s).

EXAMPLE 5

(E)-2-(4-(3-(4-Aminophenyl)propenoyl)aminobutyl)-7-trifluoromethylsulfonyloxy-1,2,3,4-tetrahydroisoquinoline A mixture of 2-(4-aminobutyl)-7-trifluoromethylsulfonyloxy-1,2,3,4-tetrahydroisoquinoline (440 mg, 1.25 mmol), trans-4-aminocinnamic acid hydrochloride (250 mg, 1.25 mmol), triethylamine (0.174 ml, 1.25 mmol) 1-ethyl-3-(3-dimethylaminopropyl)carbodiimide hydrochloride (240 mg, 1.25 mmol) and 1-hydroxybenzotriazole (100 mg, 0.74 mmol) in dichloromethane (50 ml) was stirred at room temperature for 18 h. The reaction mixture was washed with saturated aqueous sodium hydrogen carbonate (50 ml) and the organic layer dried (Na₂SO₄) and evaporated in vacuo. The residue was chromatographed on silica using 10–100% ethyl acetate-hexane gradient elution to afford the title compound (280 mg, 45%).

Mass spectrum (API⁺): Found 498 (MH⁺). $C_{23}H_{26}F_3N_3O_4S$ requires 497. ¹H NMR (CDCl₃) δ: 1.75 (4H, m), 2.55 (2H, m), 2.75 (2H, t, J=6 Hz), 2.90 (2H, t, J=6 Hz), 3.40 (2H, m), 3.65 (2H, s), 3.85 (2H, br s), 6.00 (1H, d, J=15 Hz), 6.45 (1H, m), 6.60 (2H, d, J=8 Hz), 6.95 (1H, d, J=2 Hz), 7.05 (1H, dd, J=8, 2 Hz), 7.20 (4H, m), 7.50 (1H, d, J=15 Hz).

EXAMPLE 6

(E)-2-(4-(3-(4-Nitrophenyl)propenoyl)aminobutyl)-7-trifluoromethylsulfonyloxy-1,2,3,4-tetrahydroisoquinoline A mixture of 2-(4-aminobutyl)-7-trifluoromethylsulfonyloxy-1,2,3,4-tetrahydroisoquinoline (400 mg, 1.14 mmol), trans-4-nitrocinnamoyl chloride (240 mg, 1.14 mmol) and triethylamine (0.2 ml, 1.37 mmol) in dichloromethane (6 ml) was shaken at room temperature for 18 h. Saturated aqueous potassium carbonate (5 ml) was added and shaking resumed for 15 mins. The organic layer was chromatographed on silica using 10–100% ethyl acetate-hexane gradient elution to afford the title compound as a yellow gum (490 mg, 82%).

Mass spectrum (API⁺): Found 528 (MH⁺). $C_{23}H_{24}F_3N_3O_6S$ requires 527. ¹H NMR (CDCl₃) δ: 1.75 (4H, m), 2.60 (2H, m), 2.75 (2H, t, J=6 Hz), 2.95 (2H, t, J=6 Hz), 3.45 (2H, m), 3.65 (2H, s), 6.25 (1H, d, J=15 Hz), 6.95 (2H, m), 7.05 (1H, dd, J=8, 2 Hz), 7.15 (1H, d, J=8 Hz), 7.45 (2H, d, J=8 Hz), 7.60 (1H, d, J=15 Hz), 8.20 (2H, d, J=8 Hz).

EXAMPLE 7

(E)-7-Cyano-2-(4-(3-(5-(3-dimethylaminomethyl)indolyl) propenoyl)aminobutyl)-1,2,3,4-tetrahydroisoquinoline A mixture of (E)-7-cyano-2-(4-(3-(5-indolyl)propenoyl) aminobutyl)-1,2,3,4-tetrahydroisoquinoline (0.15 g, 0.37 mmol), dimethylamine hydrochloride (0.033 g, 0.41 mmol), paraformaldehyde (0.013 g, 0.43 mmol) and 1-butanol (10 ml) was heated at reflux for 2 h. Reaction mixture was evaporated in vacuo and the residue partitioned between saturated aqueous NaHCO$_3$ (50 ml) and dichloromethane (3×30 ml). Combined organic extracts were dried (Na$_2$SO$_4$) and evaporated in vacuo to give an oil (0.13 g). Chromatography on silica using 0–10% methanol-ethyl acetate gradient elution gave the title compound (0.017 g, 13%).

Mass spectrum (API$^+$): Found 456 (MH$^+$). C$_{28}$H$_{33}$N$_5$O requires 455. $^1$H NMR (CDCl$_3$) δ: 1.70 (4H, m), 2.60 (2H, m), 2.65 (6H, s), 2.78 (2H, t, J=7 Hz), 2.97 (2H, t, J=7 Hz), 3.43 (2H, m), 3.67 (2H, s), 4.18 (2H, s), 6.32 (1H, d, J=16 Hz), 7.20 (1H, m), 7.23–7.48 (6H, m), 7.62 (1H, m), 7.70 (1H, m), 7.78 (1H, m).

What is claimed is:

1. A compound of formula (I):

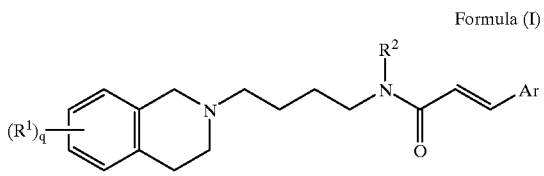

Formula (I)

wherein:
R$^1$ represents a substituent selected from: a hydrogen or halogen atom; a hydroxy, cyano, nitro, trifluoromethyl, trifluoromethoxy, trifluoromethanesulfonyloxy, C$_{1-4}$alkyl, C$_{1-4}$alkoxy, arylC$_{1-4}$alkoxy, C$_{1-4}$alkylthio, C$_{1-4}$alkoxyC$_{1-4}$alkyl, C$_{3-6}$cycloalkylC$_{1-4}$alkoxy, C$_{1-4}$alkanoyl, C$_{1-4}$alkoxycarbonyl, C$_{1-4}$alkylsulphonyl, C$_{1-4}$alkylsulphonyloxy, C$_{1-4}$alkylsulphonylC$_{1-4}$alkyl, arylsulphonyl, arylsulphonyloxy, arylsulphonylC$_{1-4}$alkyl, C$_{1-4}$alkylsulphonamido, C$_{1-4}$alkylamido, C$_{1-4}$alkylsulphonamidoC$_{1-4}$alkyl, C$_{1-4}$alkylamidoC$_{1-4}$alkyl, arylsulphonamido, arylcarboxamido, arylsulphonamidoC$_{1-4}$alkyl, arylcarboxamidoC$_{1-4}$alkyl, aroyl, aroylC$_{1-4}$alkyl, or arylC$_{1-4}$alkanoyl group; a group R$^3$OCO(CH$_2$)$_p$, R$^3$CON(R$^4$)(CH2)p, R$^3$R$^4$NCO(CH$_2$)$_p$ or R$^3$R$^4$NSO$_2$(CH$_2$)$_p$ where each of R$^3$ and R$^4$ independently represents a hydrogen atom or a C$_{1-4}$alkyl group or R$^3$R$^4$ forms part of a C$_{3-6}$azacyloalkane or C$_{3-6}$(2-oxo)azacycloalkane ring and p represents zero or an integer from 1 to 4; or a group Ar$^1$Z, wherein Ar$^1$ represents an optionally substituted phenyl ring or an optionally substituted 5- or 6-membered aromatic heterocyclic ring and Z represents a bond, O, S, or CH$_2$;

R$^2$ represents a hydrogen atom or a C$_{1-4}$alkyl group;

q is 1 or 2;

Ar represents an optionally substituted phenyl ring or an optionally substituted 5- or 6-membered aromatic heterocyclic ring; or an optionally substituted bicyclic aromatic or heteroaromatic ring system;

or a salt thereof.

2. A compound according to claim 1 wherein q represents 1.

3. A compound of formula (I) which is:
(E)-7-Methoxy-2-(4-(3-phenylpropenoyl)aminobutyl)-1,2,3,4-tetrahydroisoquinoline;
(E)-7-Hydroxy-2-(4-(3-phenylpropenoyl)aminobutyl)-1,2,3,4-tetrahydroisoquinoline;
(E)-2-(4-(3-Phenylpropenoyl)aminobutyl)-7-trifluoromethylsulfonyloxy-1,2,3,4-tetrahydroisoquinoline;
(E)-2-(4-(3-(3-Nitrophenyl)propenoyl)aminobutyl)-7-trifluoromethylsulfonyloxy-1,2,3,4-tetrahydroisoquinoline;
(E)-2-(4-(3-(4-Methoxyphenyl)propenoyl)aminobutyl)-7-trifluoromethylsulfonyloxy-1,2,3,4-tetrahydroisoquinoline;
(E)-2-(4-(3-(4-Bromophenyl)propenoyl)aminobutyl)-7-trifluoromethylsulfonyloxy-1,2,3,4-tetrahydroisoquinoline;
(E)-2-(4-(3-(2-Thienyl)propenoyl)aminobutyl)-7-trifluoromethylsulfonyloxy-1,2,3,4-tetrahydroisoquinoline;
(E)-2-(4-(3-(2-Naphthyl)propenyl)aminobutyl)-7-trifluoromethylsulfonyloxy-1,2,3,4-tetrahydroisoquinoline;
(E)-2-(4-(3-(3-Furyl)propenoyl)aminobutyl)-7-trifluoromethylsulfonyloxy-1,2,3,4-tetrahydroisoquinoline;
(E)-2-(4-(3-(4-Chlorophenyl)propenoyl)aminobutyl)-7-trifluoromethylsulfonyloxy-1,2,3,4-tetrahydroisoquinoline;
(E)-2-(4-(3-(4-Dimethylaminophenyl)propenoyl)aminobutyl)-7-trifluoromethylsulfonyloxy-1,2,3,4-tetrahydroisoquinoline;
(E)-2-(4-(3-(3,4-Methylenedioxyphenyl)propenoyl)aminobutyl)-7-trifluoromethylsulfonyloxy-1,2,3,4-tetrahydroisoquinoline;
(E)-2-(4-(3-(3-(1-Methyl)indolyl)propenoyl)aminobutyl)-7-trifluoromethylsulfonyloxy-1,2,3,4-tetrahydroisoquinoline;
(E)-2-(4-(3-(1-Naphthyl)propenoyl)aminobutyl)-7-trifluoromethylsulfonyloxy-1,2,3,4-tetrahydroisoquinoline;
(E)-2-(4-(3-(2-Methylphenyl)propenoyl)aminobutyl)-7-trifluoromethylsulfonyloxy-1,2,3,4-tetrahydroisoquinoline;
(E)-2-(4-(3-(3-Cyanophenyl)propenoyl)aminobutyl)-7-trifluoromethylsulfonyloxy-1,2,3,4-tetrahydroisoquinoline;
(E)-2-(4-(3-(2-Quinolinyl)propenoyl)aminobutyl)-7-trifluoromethylsulfonyloxy-1,2,3,4-tetrahydroisoquinoline;
(E)-2-(4-(3-(2-Methoxyphenyl)propenoyl)aminobutyl)-7-trifluoromethylsulfonyloxy-1,2,3,4-tetrahydroisoquinoline;
(E)-2-(4-(3-(3-Indolyl)propenoyl)aminobutyl)-7-trifluoromethylsulfonyloxy-1,2,3,4-tetrahydroisoquinoline;
(E)-2-(4-(3-(2-Benzofuranyl)propenoyl)aminobutyl)-7-trifluoromethylsulfonyloxy-1,2,3,4-tetrahydroisoquinoline;
(E)-2-(4-(3-(4-Acetylphenyl)propenoyl)aminobutyl)-7-trifluoromethylsulfonyloxy-1,2,3,4-tetrahydroisoquinoline;
(E)-2-(4-(3-(3-Methoxyphenyl)propenoyl)aminobutyl)-7-trifluoromethylsulfonyloxy-1,2,3,4-tetrahydroisoquinoline;
(E)-2-(4-(3-(3-Quinolinyl)propenoyl)aminobutyl)-7-trifluoromethylsulfonyloxy-1,2,3,4-tetrahydroisoquinoline;
(E)-2-(4-(3-(5-(2,3-Dihydro)benzofuranyl)propenoyl)aminobutyl)-7-trifluoromethylsulfonyloxy-1,2,3,4-tetrahydroisoquinoline;

(E)-2-(4-(3-(6-(1,4-benzodioxanyl)propenoyl)aminobutyl)-7-trifluoromethylsulfonyloxy-1,2,3,4-tetrahydroisoquinoline;

(E)-2-(4-(3-(3-Acetylphenyl)propenoyl)aminobutyl)-7-trifluoromethylsulfonyloxy-1,2,3,4-tetrahydroisoquinoline;

(E)-2-(4-(3-(3-Acetamidophenyl)propenoyl)aminobutyl)-7-trifluoromethylsulfonyloxy-1,2,3,4-tetrahydroisoquinoline;

(E)-2-(4-(3-(3-Dimethylaminophenyl)propenoyl)amninobutyl)-7-trifluoromethylsulfonyloxy-1,2,3,4-tetrahydroisoquinoline;

(E)-2-(4-(3-(2-Quinoxalinyl)propenoyl)aminobutyl)-7-trifluoromethylsulfonyloxy-1,2,3,4-tetrahydroisoquinoline;

(E)-2-(4-(3-(2-Benzothiazolyl)propenoyl)aminobutyl)-7-trifluoromethylsulfonyloxy-1,2,3,4-tetrahydroisoquinoline;

(E)-2-(4-(3-(3,4-Dichlorophenyl)propenoyl)aminobutyl)-7-trifluoromethylsulfonyloxy-1,2,3,4-tetrahydroisoquinoline;

(E)-2-(4-(3-(2-(1-Methyl)pyrrolyl)propenoyl)aminobutyl)-7-trifluoromethylsulfonyloxy-1,2,3,4-tetrahydroisoquinoline;

(E)-2-(4-(3-(5-Pyrido[2,3-b]indolyl)propenoyl)aminobutyl)-7-trifluoromethylsulfonyloxy-1,2,3,4-tetrahydroisoquinoline;

(E)-2-(4-(3-(5-(2-Dimethylamino)pyrimidinyl)propenoyl)aminobutyl)-7-trifluoromethylsulfonyloxy-1,2,3,4-tetrahydroisoquinoline;

(E)-2-(4-(3-(2-Benzoxazolyl)propenoyl)aminobutyl)-7-trifluoromethylsulfonyloxy-1,2,3,4-tetrahydroisoquinoline;

(E)-2-(4-(3-(4-(1-Pyrrolidinyl)phenyl)propenoyl)aminobutyl)-7-trifluoromethylsulfonyloxy-1,2,3,4-tetrahydroisoquinoline;

(E)-2-(4-(3-(3-Methylaminocarbonylphenyl)propenoyl)aminobutyl)-7-trifluoromethylsulfonyloxy-1,2,3,4-tetrahydroisoquinoline;

(E)-2-(4-(3-(3,4-Methylenedioxyphenyl)propenoyl)aminobutyl)-7-trifluoromethylsulfonyloxy-1,2,3,4-tetrahydroisoquinoline;

(E)-2-(4-(3-(3-Aminocarbonylphenyl)propenoyl)aminobutyl)-7-trifluoromethylsulfonyloxy-1,2,3,4-tetrahydroisoquinoline;

(E)-2-(4-(3-(2-Acetamidophenyl)propenoyl)aminobutyl)-7-trifluoromethylsulfonyloxy-1,2,3,4-tetrahydroisoquinoline;

(E)-2-(4-(3-(2-Naphthyl)propenoyl)aminobutyl)-7-(2-thiophene)sulfonyloxy-1,2,3,4-tetrahydroisoquinoline;

(E)-2-(4-(3-(4-Dimethylaminophenyl)propenoyl)aminobutyl)-7-(2-thiophene)sulfonyloxy-1,2,3,4-tetrahydroisoquinoline;

(E)-2-(4-(3-(2-Naphthyl)propenoyl)aminobutyl)-7-methylsulfonyloxy-1,2,3,4-tetrahydroisoquinoline;

(E)-2-(4-(3-(4-Dimethylaminophenyl)propenoyl)aminobutyl)-7-methylsulfonyloxy-1,2,3,4-tetrahydroisoquinoline;

(E)-2-(4-(3-(2-Naphthyl)propenoyl)aminobutyl)-7-acetyl-1,2,3,4-tetrahydroisoquinoline;

(E)-2-(4-(3-(2-Naphthyl)propenoyl)aminobutyl)-7-bromo-1,2,3,4-tetrahydroisoquinoline;

(E)-2-(4-(3-(2-Naphthyl)propenoyl)aminobutyl)-7-(4-cyanophenyl)sulfonyloxy-1,2,3,4-tetrahydroisoquinoline;

(E)-2-(4-(3-(2-Naphthyl)propenoyl)aminobutyl)-7-methoxy-1,2,3,4-tetrahydroisoquinoline;

(E)-7-Phenylsulfonylmethyl-2-(4-(3-(2-naphthyl)propenoly)aminobutyl)-1,2,3,4-tetrahydroisoquinoline;

(E)-7-Methylsulfonamido-2-(4-(3-(2-naphthyl)propenoly)aminobutyl)-1,2,3,4-tetrahydroisoquinoline;

(E)-2-(4-(3-(2-Naphthyl)propenoyl)aminobutyl)-7-phenylsulfonamido-1,2,3,4-tetrahydroisoquinoline;

(E)-7-(4-Cyanophenyl)sulfonamido-2-(4-(3-(2-naphthyl)propenoly)aminobutyl)-1,2,3,4-tetrahydroisoquinoline;

(E)-2-(4-(3-(5-Indolyl)propenoyl)aminobutyl)-7-trifluoromethylsulfonyloxy-1,2,3,4-tetrahydroisoquinoline;

(E)-2-(4-(3-(5-Benzimidazolyl)propenoly)aminobutyl)-7-trifluoromethylsulfonyloxy-1,2,3,4-tetrahydroisoquinoline;

(E)-7-Methylsulfonylmethyl-2-(4-(3-(2-naphthyl)propenoly)aminobutyl)-1,2,3,4-tetrahydroisoquinoline;

(E)-2-(4-(3-(2-Naphthyl)propenoly)aminobutyl)-7-trifluoromethoxy-1,2,3,4-tetrahydroisoquinoline;

(E)-7-Cyano-2-(4-(3-(2-naphthyl)propenoly)aminobutyl)-1,2,3,4-tetrahydroisoquinoline;

(E)-2-(4-(3-(3-Indolyl)propenoly)aminobutyl)-7-trifluoromethoxy-1,2,3,4-tetrahydroisoquinoline;

(E)-2-(4-(3-(4-Dimethylaminophenyl)propenoly)-7-trifluoromethoxy-1,2,3,4-tetrahydroisoquinoline;

(E)-2-(4-(3-(4-Aminophenyl)propenoly)aminobutyl)-7-trifluoromethylsulfonyloxy-1,2,3,4-tetrahydroisoquinoline;

(E)-2-(4-(3-(4-Nitrophenyl)propenoly)aminobutyl)-7-trifluoromethylsulfonyloxy-1,2,3,4-tetrahydroisoquinoline;

(E)-7-Cyano-2-(4-(3-(3-indolyl)propenoyl)aminobutyl)-1,2,3,4-tetrahydroisoquinoline;

(E)-2-(4-(3-(3-(7-Methyl)indolyl)propenoyl)aminobutyl)-7-trifluoromethylsulfonyloxy-1,2,3,4-tetrahydroisoquinoline;

(E)-2-(4-(3-(2-(6-Acetyl)naphthyl)propenoyl)aminobutyl)-7-trifluoromethylsulfonyloxy-1,2,3,4-tetrahydroisoquinoline;

(E)-7-Cyano-2-(4-(3-(3-(7-methyl)indolyl)propenoyl)aminobutyl)-1,2,3,4-tetrahydroisoquinoline;

(E)-7-Cyano-2-(4-(3-(5-benzimidazolyl)propenoyl)aminobutyl)-1,2,3,4-tetrahydroisoquinoline;

(E)-7-Cyano-2-(4-(3-(5-indolyl)propenoyl)aminobutyl)-1,2,3,4-tetrahydroisoquinoline;

(E)-2-(4-(3-(2-(6-Acetyl)naphthyl)propenoyl)aminobutyl)-7-cyano-1,2,3,4-tetrahydroisoquinoline;

(E)-7-Cyano-2-(4-(3-(6-indolyl)propenoyl)aminobutyl)-1,2,3,4-tetrahydroisoquinoline;

(E)-7-Cyano-2-(4-(3-(3-(7-fluoro)indolyl)propenoyl)aminobutyl)-1,2,3,4-tetrahydroisoquinoline;

(E)-2-(4-(3-(3-(7-Bromo)indolyl)propenoyl)aminobutyl)-7-trifluoromethoxy-1,2,3,4-tetrahydroisoquinoline;

(E)-2-(4-(3-(3-(7-Bromo)indolyl)propenoyl)aminobutyl)-7-cyano-1,2,3,4-tetrahydroisoquinoline;

(E)-2-(4-(3-(3-(7-Cyano)indolyl)propenoyl)aminobutyl)-7-cyano-1,2,3,4-tetrahydroisoquinoline;

(E)-7-Cyano-2-(4-(3-(5-(2-methyl)indolyl)propenoyl)aminobutyl)-1,2,3,4-tetrahydroisoquinoline;

(E)-2-(4-(3-(5-(2-Methyl)indolyl)propenoyl)aminobutyl)-7-trifluoromethoxy-1,2,3,4-tetrahydroisoquinoline;

(E)-2-(4-(3-(3-(7-Acetyl)indolyl)propenoyl)aminobutyl)-7-cyano-1,2,3,4-tetrahydroisoquinoline;

(E)-7-Cyano-2-(4-(3-(6-(2-methyl)indolyl)propenoyl)aminobutyl)-1,2,3,4-tetrahydroisoquinoline;

(E)-7-Cyano-2-(4-(3-(5-(2,3-dihydro-2-oxo)-1H-indolyl)propenoyl)aminobutyl)-1,2,3,4-tetrahydroisoquinoline;

(E)-2-(4-(3-(6-(1,2-Dihydro-2-oxo)quinolinyl)propenoyl)aminobutyl)-7-trifluoromethoxy-1,2,3,4-tetrahydroisoquinoline;

(E)-2-(4-(3-(5-(2-Acetyl)indolyl)propenoyl)aminobutyl)-7-cyano-1,2,3,4-tetrahydroisoquinoline;

(E)-7-Chloro-2-(4-(3-(6-indolyl)propenoyl)aminobutyl)-1,2,3,4-tetrahydroisoquinoline;

(E)-7-Cyano-2-(4-(3-(5-(3-methyl)indolyl)propenyl)aminobutyl)-1,2,3,4-tetrahydroisoquinoline;

(E)-2-(4-(3-(6-(3-Methyl)indolyl)propenoyl)aminobutyl)-7-trifluoromethoxy-1,2,3,4-tetrahydroisoquinoline;

(E)-7-Cyano-2-(4-(3-(5-(1-methyl)indolyl)propenoyl)aminobutyl)-1,2,3,4-tetrahydroisoquinoline;

(E)-2-(4-(3-(2-(1-Methyl)indolyl)propenoyl)aminobutyl)-7-trifluoromethylsulfonyloxy-1,2,3,4-tetrahydroisoquinoline;

(E)-2-(4-(3-(5-Indolyl)propenoyl)aminobutyl)-1,2,3,4-tetrahydroisoquinoline;

(E)-7-Cyano-2-(4-(3-(5-(2-methyl)benzimidazolyl)propenoyl)aminobutyl)-1,2,3,4-tetrahydroisoquinoline;

(E)-2-(4-(3-(5-(2-Methyl)benzimidazolyl)propenoyl)aminobutyl)-7-trifluoromethoxy-1,2,3,4-tetrahydroisoquinoline;

(E)-2-(4-(3-(5-Indolyl)propenoyl)aminobutyl)-7-trifluoromethyl-1,2,3,4-tetrahydroisoquinoline;

(E)-2-(4-(3-(5-Indolyl)propenoyl)aminobutyl)-7-methylsulfonamido-1,2,3,4-tetrahydroisoquinoline;

(E)-2-(4-(3-(5-Indolyl)propenoyl)aminobutyl)-7-methylaminosulfonyl-1,2,3,4-tetrahydroisoquinoline;

(E)-2-(4-(3-(3-(7-Methyl)indolyl)propenoyl)aminobutyl)-7-trifluoromethoxy-1,2,3,4-tetrahydroisoquinoline;

(E)-7-Cyano-2-(4-(3-(5-(3-dimethylaminomethyl)indolyl)propenoyl)aminobutyl)-1,2,3,4-tetrahydroisoquinoline;

or a salt thereof.

4. A process for preparing a compound of formula (I) as defined in claim 1 which process comprises:

(a) reacting a compound of formula (II):

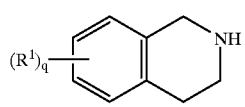

Formula (II)

wherein $R^1$ and q are as hereinbefore defined;

with a compound of formula (III):

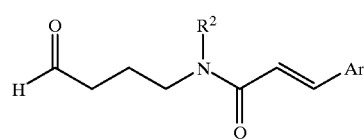

Formula (III)

wherein $R^2$ and Ar are as hereinbefore defined;

(b) reaction of a compound of formula (IV):

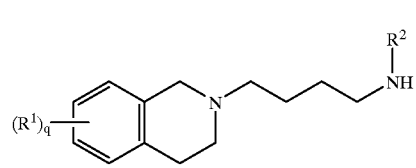

Formula (IV)

wherein $R^1$ and $R^2$ are as hereinbefore defined;

with a compound of formula (V):

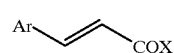

Formula (V)

wherein Ar is as hereinbefore defined and X is a halogen atom or the residue of an activated ester;

(c) to prepare a compound of formula (I) wherein $R^1$ is $Ar^1$—Z and Z is a bond, reacting a compound of formula (VI):

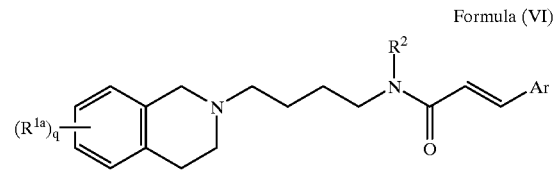

Formula (VI)

wherein one $R^{1a}$ represents a group W wherein W is a halogen atom or a trifluoromethylsulphonyloxy group, or W is a group M selected from a boron derivative e.g. a boronic acid function $B(OH)_2$ or a metal function such as trialkyl-stannyl e.g. $SnBu_3$, zinc halide or magnesium halide, and when q is 2 the other $R^{1a}$ is $R^1$; with a compound $Ar^1$—$W^1$, wherein $W^1$ is a halogen atom or a trifluoromethylsulphonyloxy group when W is a group M or $W^1$ is a group M when W is a halogen atom or a trifluoromethylsulphonyloxy group;

(d) to prepare a compound of formula (I) wherein $R^1$ is $Ar^1$—Z and Z is O or S, reacting a compound of formula (VII):

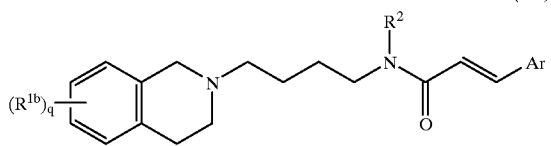

Formula (VII)

wherein one $R^{1b}$ represent a group ZH and when q is 2 the other $R^{1b}$ represents $R^1$; with a reagent serving to introduce the group $Ar^1$;

(e) interconversion of one compound of formula (I) to a different compound of formula (I) e.g. (i) alkylation of a compound (I) wherein $R^2$ represent hydrogen, (ii) conversion of one $R^1$ from alkoxy (e.g.methoxy) to hydroxy, or (iii) conversion of $R^1$ from hydroxy to sulphonyloxy, eg alkylsulphonyloxy or trifluoromethanesulphonyloxy; optionally thereafter forming a salt of formula (I).

5. A pharmaceutical composition comprising a compound of formula (I) as claimed in claim 1 or a physiologically acceptable salt thereof and a physiologically acceptable carrier therefor.

6. A method of treating a psychotic condition which requires modulation of a dopamine receptor which comprises administering to a subject in need thereof an effective amount of a compound of formula (I) as claimed in claim 1 or a physiologically acceptable salt thereof.

7. The method according to claim 6, wherein the dopamine receptor is a dopamine $D_3$ receptor.

8. The method according to claim 7, wherein a dopamine antagonist is required.

9. A method of treating a drug dependency condition which requires modulation of a dopamine receptor which comprises administering to a subject in need thereof an effective amount of a compound of formula (I) as claimed in claim 1 or a physiologically acceptable salt thereof.

10. The method of claim 9, wherein the dopamine receptor is a dopamine $D_3$ receptor.

* * * * *